(12) United States Patent
Mirmira

(10) Patent No.: US 11,268,148 B2
(45) Date of Patent: Mar. 8, 2022

(54) DNA METHYLATION IN INFLAMMATORY DISEASE

(71) Applicant: INDIANA UNIVERSITY RESEARCH AND TECHNOLOGY CORPORATION, Indianapolis, IN (US)

(72) Inventor: Raghavendra G. Mirmira, Zionsville, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 107 days.

(21) Appl. No.: 16/444,850

(22) Filed: Jun. 18, 2019

(65) Prior Publication Data

US 2019/0316202 A1    Oct. 17, 2019

Related U.S. Application Data

(63) Continuation-in-part of application No. PCT/US2017/066708, filed on Dec. 15, 2017.

(60) Provisional application No. 62/436,137, filed on Dec. 19, 2016.

(51) Int. Cl.
| | | |
|---|---|---|
| *C12Q 1/68* | (2018.01) | |
| *C07H 21/04* | (2006.01) | |
| *C12Q 1/6883* | (2018.01) | |
| *G16B 35/20* | (2019.01) | |

(52) U.S. Cl.
CPC ........... *C12Q 1/6883* (2013.01); *G16B 35/20* (2019.02); *C12Q 2600/154* (2013.01)

(58) Field of Classification Search
None
See application file for complete search history.

(56) References Cited

U.S. PATENT DOCUMENTS

| | | |
|---|---|---|
| 2003/0031654 A1 | 2/2003 | Gorman |
| 2010/0227325 A1 | 9/2010 | Vilanova |
| 2010/0292131 A1 | 11/2010 | Kas |
| 2018/0230539 A1* | 8/2018 | Mirmira ................ C12Q 1/6883 |

FOREIGN PATENT DOCUMENTS

WO    WO-2017015497 A2 *   1/2017   ........... C12Q 1/6883

OTHER PUBLICATIONS

Zhang et al. (Hepatol Int, vol. 7, pp. 893-900, 2013). (Year: 2013).*
Fradin et al. (PLoS Once, vol. 7, No. 5 e36278, May 2012). (Year: 2012).*
Ogihara T, Mirmira RG. An islet in distress: β cell failure in type 2 diabetes. J Diab Invest. Aug. 2010;1:123-33.
Bacha F, Lee S, Gungor N, Arslanian SA. From Pre-Diabetes to Type 2 Diabetes in Obese Youth. Diabetes Care. Oct. 2010;33(10):2225-31.
Giannini C, Weiss R, Cali A, Bonadonna R, Santoro N, Pierpont B, et al. Evidence for Early Defects in Insulin Sensitivity and Secretion Before the Onset of Glucose Dysregulation in Obese Youths. Diabetes. Mar. 2012;61(3):606-14.
Kahn SE, Prigeon RL, McCulloch DK, Boyko EJ, Bergman RN, Schwartz MW, et al. Quantification of the Relationship Between Insulin Sensitivity and β-Cell Function in Human Subjects: Evidence for a Hyperbolic Function. Diabetes. Nov. 1, 1993;42(11):1663-72.
The Diabetes Prevention Program Research Group. Role of Insulin Secretion and Sensitivity in the Evolution of Type 2 Diabetes in the Diabetes Prevention Program Effects of Lifestyle Intervention and Metformin. Diabetes. Aug. 1, 2005;54(8):2404-14.
Butler AE, Janson J, Bonner-Weir S, Ritzel R, Rizza RA, Butler PC. Beta-cell deficit and increased beta-cell apoptosis in humans with type 2 diabetes. Diabetes. Jan. 2003;52(1):102-10.
Mclean N, Ogilvie RF. Quantitative estimation of the pancreatic islet tissue in diabetic subjects. Diabetes. 1955;4:367-76.
White MG, Marshall HL, Rigby R, Huang GC, Amer A, Booth T, et al. Expression of Mesenchymal and α-Cell Phenotypic Markers in Islet β-Cells in Recently Diagnosed Diabetes. Diabetes Care. Nov. 1, 2013;36(11):3818-20.
Talchai C, Xuan S, Lin HV, Sussel L, Accili D. Pancreatic β Cell Dedifferentiation as a Mechanism of Diabetic β Cell Failure. Cell. Sep. 2012;150(6):1223-34.
Fisher MM, Watkins RA, Blum J, Evans-Molina C, Chalasani N, DiMeglio LA, et al. Elevations in Circulating Methylated and Unmethylated Preproinsulin DNA in New-Onset Type 1 Diabetes. Diabetes. Nov. 2015;64(11):3867-72.
Herold KC, Usmani-Brown S, Ghazi T, Lebastchi J, Beam CA, Bellin MD, et al. β cell death and dysfunction during type 1 diabetes development in at-risk individuals. J Clin Invest. Mar. 2, 2015;125(3):1163-73.
Husseiny MI, Kaye A, Zebadua E, Kandeel F, Ferreri K. Tissue-Specific Methylation of Human Insulin Gene and PCR Assay for Monitoring Beta Cell Death. PLoS ONE. Apr. 4, 2014):e94591.
Lehmann-Werman R, Neiman D, Zemmour H, Moss J, Magenheim J, Vaknin-Dembinsky A, et al. Identification of tissue-specific cell death using methylation patterns of circulating DNA. Proc Natl Acad Sci USA. Mar. 29, 2016;113(13):E1826-1834.
Fisher MM, Perez Chumbiauca CN, Mather KJ, Mirmira RG, Tersey SA. Detection of islet beta-cell death in vivo by multiplex PCR analysis of differentially methylated DNA. Endocrinology. Sep. 2013;154(9):3476-81.

(Continued)

*Primary Examiner* — Jeanine A Goldberg
(74) *Attorney, Agent, or Firm* — Barnes & Thornburg LLP

(57) ABSTRACT

Disclosed herein are methods for determining inflammation in subjects. Also disclosed are methods for determining whether a subject has sepsis. The methods include determining methylation of preproinsulin DNA and chromatin target of PRMT1 (CHTOP).

5 Claims, 23 Drawing Sheets

Specification includes a Sequence Listing.

(56) References Cited

OTHER PUBLICATIONS

Evans-Molina C, Robbins RD, Kono T, Tersey SA, Vestermark GL, Nunemaker CS, et al. PPAR-{gamma} Activation Restores Islet Function in Diabetic Mice Through Reduction of ER Stress and Maintenance of Euchromatin Structure. Mol Cell Biol. May 2009;29:2053-67.

Rui J, Deng S, Lebastchi J, Clark PL, Usmani-Brown S, Herold KC. Methylation of insulin DNA in response to proinflammatory cytokines during the progression of autoimmune diabetes in NOD mice. Diabetologia. May 2016;59(5):1021-9.

Butler AE, Dhawan S, Hoang J, Cory M, Zeng K, Fritsch H, et al. Beta-cell deficit in Obese Type 2 Diabetes, a Minor Role of Beta-cell Dedifferentiation and Degranulation. J Clin Endocrinol Metab. Dec. 23, 2015;jc.2015-3566.

Schubeler D. Function and information content of DNA methylation. Nature. Jan. 15, 2015;517(7534):321-6.

Kuroda A, Rauch TA, Todorov I, Ku HT, Al-Abdullah IH, Kandeel F, et al. Insulin gene expression is regulated by DNA methylation. PloS One. 2009;4(9):e6953.

Singh T, Newman AB. Inflammatory markers in population studies of aging. Ageing Res Rev. Jul. 2011;10(3):319-29.

Yang BT, Dayeh TA, Kirkpatrick CL, Taneera J, Kumar R, Groop L, et al. Insulin promoter DNA methylation correlates negatively with insulin gene expression and positively with HbA1c levels in human pancreatic islets. Diabetologia. Nov. 23, 2010;54:360-7.

Michaliszyn SF, Mari A, Lee S, Bacha F, Tfayli H, Farchoukh L, et al. β-cell function, incretin effect, and incretin hormones in obese youth along the span of glucose tolerance from normal to prediabetes to type 2 diabetes. Diabetes. Nov. 2014;63(11):3846-55.

Burns SF, Bacha F, Lee SJ, Tfayli H, Gungor N, Arslanian SA. Declining β-cell function relative to insulin sensitivity with escalating OGTT 2-h glucose concentations in the nondiabetic through the diabetic range in overweight youth. Diabetes Care. Sep. 2011;34(9):2033-40.

Tfayli H, Bacha F, Gungor N, Arslanian S. Islet cell antibody-positive versus-negative phenotypic type 2 diabetes in youth: does the oral glucose tolerance test distinguish between the two? Diabetes Care. Mar. 2010;33(3):632-8.

George L, Bacha F, Lee S, Tfayli H, Andreatta E, Arslanian S. Surrogate estimates of insulin sensitivity in obese youth along the spectrum of glucose tolerance from normal to prediabetes to diabetes. J Clin Endocrinol Metab. Jul. 2011;96(7):2136-45.

Sjaarda L, Lee S, Tfayli H, Bacha F, Bertolet M, Arslanian S. Measuring β-cell function relative to insulin sensitivity in youth: does the hyperglycemic clamp suffice? Diabetes Care. Jun. 2013;36(6):1607-12.

Scharfmann R, Pechberty S, Hazhouz Y, Bülow M von, Bricout-Neveu E, Grenier-Godard M, et al. Development of a conditionally immortalized human pancreatic β cell line. J Clin Invest. May 1, 2014;124(124(5)):2087-98.

Maier B, Ogihara T, Trace AP, Tersey SA, Robbins RD, Chakrabarti SK, et al. The unique hypusine modification of eIF5A promotes islet beta cell inflammation and dysfunction in mice. J Clin Invest. Jun. 2010;120(6):2156-70.

Fisher et al. Elevations in Circulating Methylated and Unmethylated Preproinsulin DNA in New-Onset Type 1 Diabetes. Diabetes, 2015, vol. 64, No. 11, pp. 3867-3872; abstract; p. 3868, col. 1, second paragraph, third paragraph, fifth paragraph. DOI: 10.2337/db15-0430.

Fisher et al. Detection of Islet B-Cell Death In Vivo By Multiplex PCR Analysis of Differentially Methylated DNA. Endocrinology, 2013, vol. 154, No. 9; pp. 3476-3481; abstract; p. 3477, col. 2, 182. DOI: 10.1210/en.2013-1223.

Quan et al. Role of Pancreatic B-Cell Death and Inflammation in Diabetes. Diabetes, Obesity and Metabolism• 2013, vol. 15, No. s3, pp. 141-151; abstract. DOI: 10.1111/dom.12153.

International Search Report and Written Opinion dated Mar. 7, 2018 for International Application No. PCT/US17/66708.

\* cited by examiner

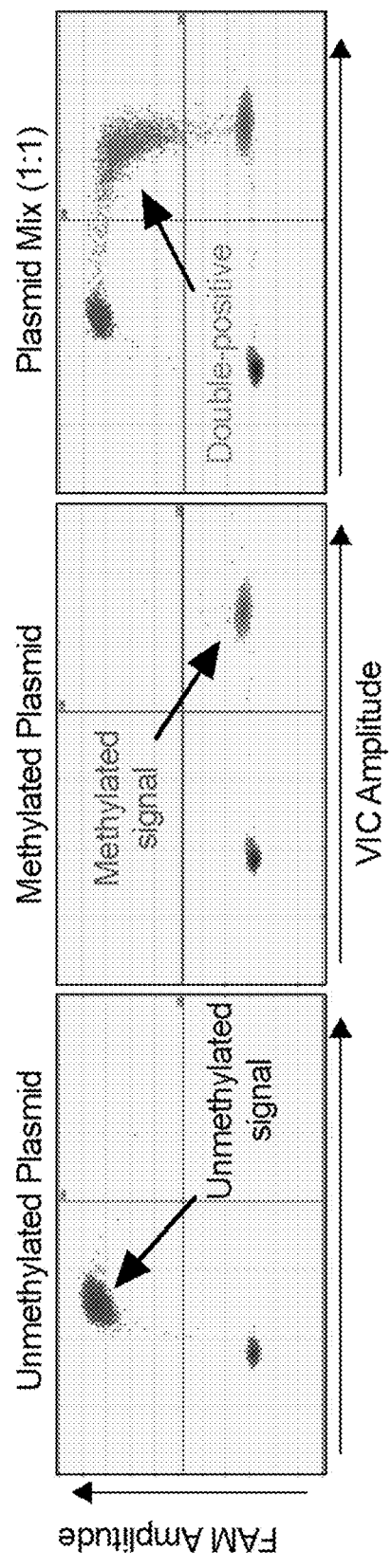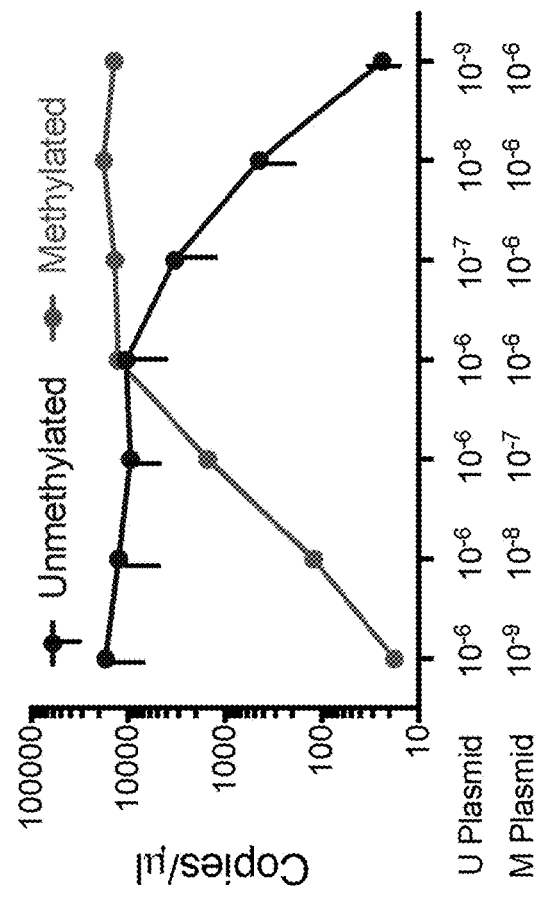
FIG. 1A
FIG. 1B

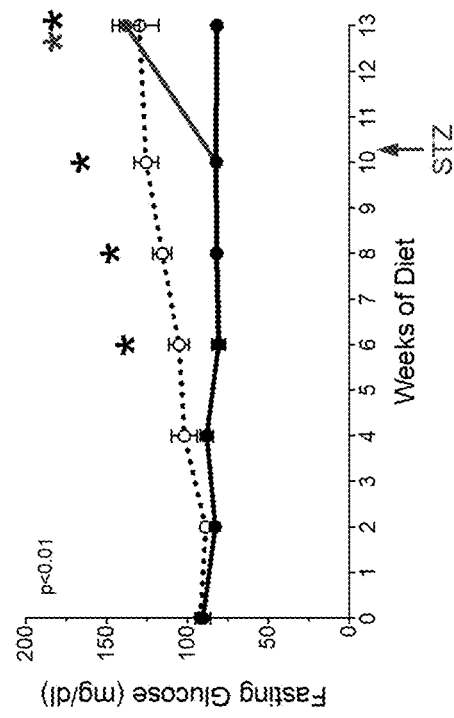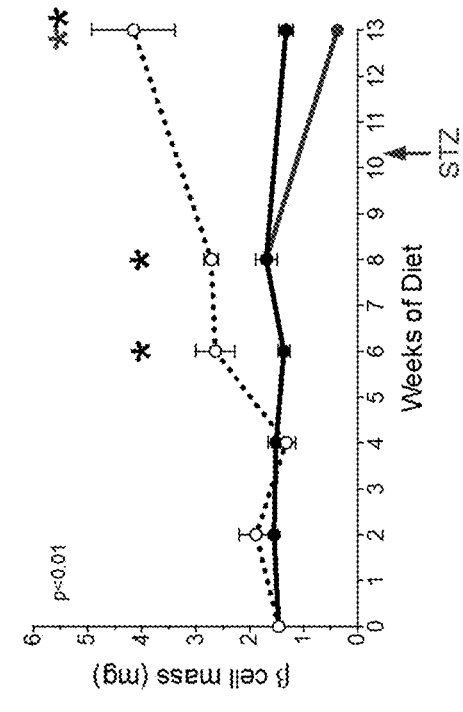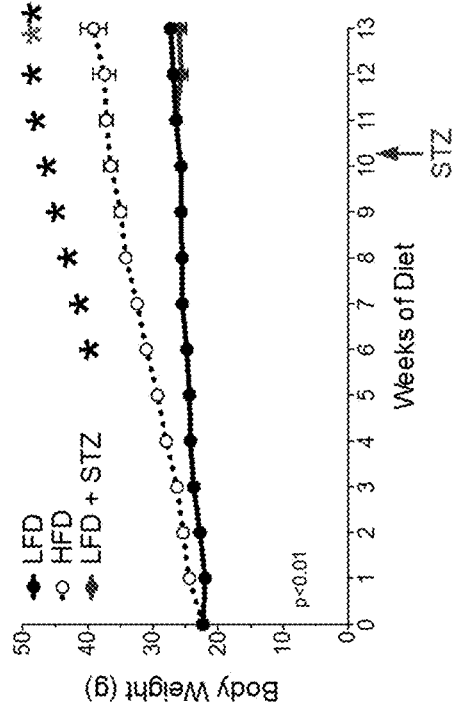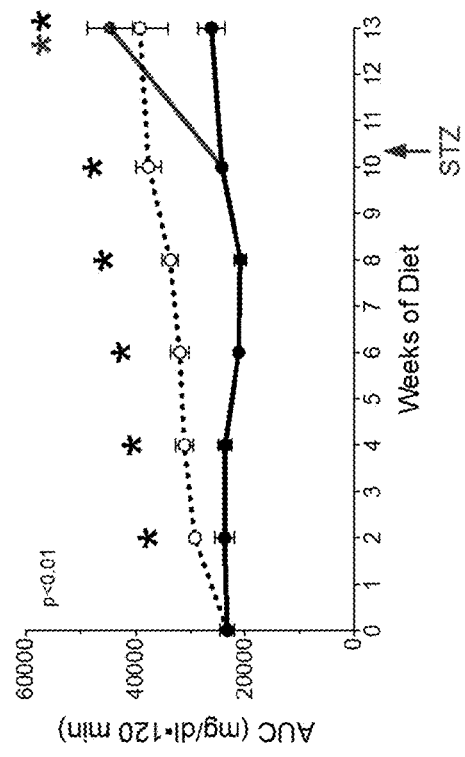

SEQUENCE LISTING

```
<160> NUMBER OF SEQ ID NOS: 22

<210> SEQ ID NO 1
<211> LENGTH: 32
<212> TYPE: DNA
<213> ORGANISM: Artificial Sequence
<220> FEATURE:
<223> OTHER INFORMATION: Synthetic

<400> SEQUENCE: 1
ggaaattgta gttttagttt ttagttattt gt                            32

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2
aaaacccatc tcccctacct atca                                     24

<210> SEQ ID NO 3
<211> LENGTH: 16
<212> TYPE: DNA
<213> ORGANISM: Artificial Sequence
<220> FEATURE:
<223> OTHER INFORMATION: Synthetic

<400> SEQUENCE: 3
acccctaccg cctaac                                              16

<210> SEQ ID NO 4
<211> LENGTH: 16
<212> TYPE: DNA
<213> ORGANISM: Artificial Sequence
```

```
<220> FEATURE:
<223> OTHER INFORMATION: Synthetic

<400> SEQUENCE: 4 accccctacca cctaac                                                        16

<210> SEQ ID NO 5
<211> LENGTH: 42
<212> TYPE: DNA
<213> ORGANISM: Artificial Sequence
<220> FEATURE:
<223> OTHER INFORMATION: Synthetic

<400> SEQUENCE: 5
aattggttta ttaggttatt agggttttt gttaagattt ta                             42

<210> SEQ ID NO 6
<211> LENGTH: 32
<212> TYPE: DNA
<213> ORGANISM: Artificial Sequence
<220> FEATURE:
<223> OTHER INFORMATION: Synthetic

<400> SEQUENCE: 6
actaaaacta caatttccaa acacttccct aa                                       32

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
ctcattaaac gtcaacacc                                                      19

<210> SEQ ID NO 8
<211> LENGTH: 19
<212> TYPE: DNA
<213> ORGANISM: Artificial Sequence
<220> FEATURE:
<223> OTHER INFORMATION: Synthetic

<400> SEQUENCE: 8
ctcattaaac atcaacacc                                                      19

<210> SEQ ID NO 9
<211> LENGTH: 4992
<212> TYPE: DNA
<213> ORGANISM: Homo sapiens

<400> SEQUENCE: 9 ctcgagggc ctagacattg ccctccagag agagcaccca acaccctcca ggcttgaccg          60
gccagggtgt ccccttccta ccttggagag agcagcccca gggcatcctg caggggtgc         120 tgggacacca gctggccttc aaggtctctg cctccctcca gccaccccac tacacgctgc        180
tgggatcctg gatctcagct ccctggccga caacactggc aaactcctac tcatccacga        240
aggccctcct gggcatggtg gtccttccca gcctggcagt ctgttcctca cacaccttgt       300
tagtgcccag ccctgaggt tgcagctggg ggtgtctctg aagggctgtg agccccagg         360 aagccctggg gaagtgcctg ccttgcctcc cccggcccct gccagcgcct ggctctgccc        420
tcctacctgg gctccccca tccagcctcc ctccctacac actcctctca aggaggcacc        480
```

-continued

```
catgtcctct ccagctgccg ggcctcagag cactgtggcg tcctgggca gccaccgcat      540
gtcctgctgt ggcatggctc agggtggaaa gggcggaagg gagggtcct gcagatagct      600
ggtgcccact accaaacccg ctcggggcag gagagccaaa ggctgggtgt gtgcagagcg      660
gccccgagag gttccgaggc tgaggccagg gtgggacata gggatgcgag gggccggggc      720
acaggatact ccaacctgcc tgccccatg gtctcatcct cctgcttctg ggacctcctg       780
atcctgcccc tggtgctaag aggcaggtaa ggggctgcag gcagcagggc tcggagccca      840
tgcccctca ccatgggtca ggctggacct ccaggtgcct gttctgggga gctgggaggg       900
ccggaggggt gtaccccagg ggctcagccc agatgacact atgggggtga tggtgtcatg      960
ggacctggcc aggagagggg agatgggctc ccagaagagg agtgggggct gagagggtgc     1020
ctggggggcc aggacggagc tgggccagtg cacagcttcc cacacctgcc cacccccaga     1080
gtcctgccgc caccccccaga tcacacggaa gatgaggtcc gagtggcctg ctgaggactt     1140
gctgcttgtc cccaggtccc caggtcatgc cctccttctg ccaccctggg gagctgaggg     1200
cctcagctgg ggctgctgtc ctaaggcagg gtgggaacta gcagccagc agggagggga      1260
cccctccctc actcccactc tcccacccc accaccttgg cccatccatg gcggcatctt      1320
gggccatccg ggactgggga cagggtcct ggggacaggg gtccggggac agggtcctgg      1380
ggacaggggt gtgggacag gggtctgggg acagggtgt ggggacaggg gtgtggggac       1440
aggggtctgg ggacaggggt gtgggacag gggtccgggg acaggggtgt ggggacaggg     1500
gtctggggac aggggtgtgg ggacaggggt gtgggacag gggtctgggg acaggggtgt      1560
ggggacaggg gtcctgggga caggggtgtg gggacaggg tgtggggaca ggggtgtggg      1620
gacaggggtg tggggacagg ggtcctgggg ataggggtgt ggggacaggg gtgtggggac      1680
aggggtcccg ggacaggggg tgtgggaca ggggtgtggg gacaggggtc ctggggacag      1740
gggtctgagg acaggggtgt gggcacaggg gtcctgggga caggggtcct ggggacaggg     1800
gtcctgggga caggggtctg ggacagcag cgcaaagagc cccgcccctgc agcctccagc     1860
tctcctggtc taatgtggaa agtggcccag gtgagggctt tgctctcctg gagacatttg      1920
cccccagctg tgagcaggga caggtctggc caccgggccc ctggttaaga ctctaatgac      1980
ccgctggtcc tgaggaagag gtgctgacga ccaaggagat cttcccacag acccagcacc     2040
agggaaatgg tccggaaatt gcagcctcag cccccagcca tctgccgacc ccccacccc       2100
gccctaatgg gccaggcggc aggggttgac aggtagggga gatgggctct gagactataa      2160
agccagcggg ggcccagcag ccctcagccc tccaggacag gctgcatcag aagaggccat     2220
caagcaggtc tgttccaagg gcctttgcgt caggtgggct cagggttcca gggtggctgg      2280
acccccaggcc ccagctctgc agcagggagg acgtggctgg gctcgtgaag catgtggggg     2340
tgagcccagg ggccccaagg cagggcacct ggccttcagc ctgcctcagc cctgcctgtc      2400
tcccagatca ctgtccttct gccatggccc tgtggatgcg cctcctgccc ctgctggcgc     2460
tgctggccct ctggggacct gacccagccg cagcctttgt gaaccaacac ctgtgcggct     2520
cacacctggt ggaagctctc tacctagtgt gcggggaacg aggcttcttc tacacaccca    2580
agacccgccg ggaggcagag gacctgcagg gtgagccaac cgcccattgc tgcccctggc     2640
cgcccccagc caccccctgc tcctggcgct cccacccagc atgggcagaa ggggcagga      2700
ggctgccacc cagcagggggg tcaggtgcac tttttttaaaa agaagttctc ttggtcacgt   2760
cctaaaagtg accagctccc tgtggcccag tcagaatctc agcctgagga cggtgttggc    2820
ttcggcagcc ccgagataca tcagagggtg ggcacgctcc tccctccact cgccccctcaa    2880
```

```
acaaatgccc cgcagcccat ttctccaccc tcatttgatg accgcagatt caagtgtttt    2940
gttaagtaaa gtcctgggtg acctggggtc acagggtgcc ccacgctgcc tgcctctggg    3000
cgaacacccc atcacgcccg gaggagggcg tggctgcctg cctgagtggg ccagacccct    3060
gtcgccagcc tcacggcagc tccatagtca ggagatgggg aagatgctgg ggacaggccc    3120
tggggagaag tactgggatc acctgttcag gctcccactg tgacgctgcc ccggggcggg    3180
ggaaggaggt gggacatgtg ggcgttgggg cctgtaggtc cacacccagt gtgggtgacc    3240
ctccctctaa cctgggtcca gcccggctgg agatgggtgg gagtgcgacc tagggctggc    3300
gggcaggcgg gcactgtgtc tccctgactg tgtcctcctg tgtccctctg cctcgccgct    3360
gttccggaac ctgctctgcg cggcacgtcc tggcagtggg gcaggtggag ctgggcgggg    3420
gccctggtgc aggcagcctg cagcccttgg ccctggaggg gtccctgcag aagcgtggca    3480
ttgtggaaca atgctgtacc agcatctgct ccctctacca gctggagaac tactgcaact    3540
agacgcagcc tgcaggcagc cccacacccg ccgcctcctg caccgagaga gatggaataa    3600
agcccttgaa ccagccctgc tgtgccgtct gtgtgtcttg ggggccctgg gccaagcccc    3660
acttcccggc actgttgtga gcccctccca gctctctcca cgctctctgg gtgcccacag    3720
gtgccaacgc caggcaggcc cagcatgcag tggctctccc caaagcggcc atgcctgttg    3780
gctgcctgct gcccccaccc tgtggctcag ggtccagtat gggagcttcg ggggtctctg    3840
aggggccagg gatggtgggg ccactgagaa gtgactctgt cagtagccga cctggagtcc    3900
ccagagacct tgttcaggaa agggaatgag aacattccag caattttccc cccacctagc    3960
cctcccaggt tctattttta gagttatttc tgatggagtc cctgtggagg gaggaggctg    4020
ggctgaggga gggggtcctg cagggcgggg ggctgggaag gtggggagag gctgccgaga    4080
gccacccgct atccccagct ctgggcagcc ccgggacagt cacacaccct ggcctcgcgg    4140
cccaagctgg cagccgtctg cagccacagc ttatgccagc ccaggtccag ccagacacct    4200
gagggaccca ctggtgcctt ggaggaagca ggagaggtca gatggcacca tgagctgggg    4260
caggtgcagg gaccgtggca gcacctggca gggcctcaga acccatgcct tgggcacccc    4320
ggccatgagg ccctgaggat tgcagcccaa gagaagcagg gaacgccagg gccacagggg    4380
cagagaccag gccagggtcc cttgcggccc ttagcccacc ccctcccagt aagcaggggc    4440
tgcttggcta ggcttccttt tgctacagac ctgctgctca cccagaggcc cacgggccct    4500
agtgacaagg tcgttgtggc tccaggtcct tggggtcct gacacagagc ctcttctgca    4560 gcaccctga ggacagggtg ctccgctggg cacccagcct agtgggcaga cgagaaccta    4620
ggggctgcct gggcctactg tggcctggga ggtcagcggg tgaccctagc taccctgtgg    4680
ctgggccagt ctgcctgcca cccaggccaa accaatctgc acctttcctg agagctccac    4740
ccagggctgg gctggggatg gctgggcctg gggctggcat gggctgtggc tgcagaccac    4800
tgccagcttg ggcctcgagg ccaggagctc accctccagc tgcccccgcct ccagagtggg    4860 ggccagggct gggcaggcgg gtggacggcc ggacactggc cccggaagag gagggaggcg    4920
gtggctggga tcggcagcag ccgtccatgg gaacacccag ccggccccac tcgcacgggt    4980
agagacaggc gc                                                        4992

<210> SEQ ID NO 10
<211> LENGTH: 36
<212> TYPE: DNA
<213> ORGANISM: Artificial Sequence
<220> FEATURE:
```

<223> OTHER INFORMATION: Synthetic primer

<400> SEQUENCE: 10
tttggagttt ttggtttagt aagttatgaa aatgtt        36

<210> SEQ ID NO 11
<211> LENGTH: 39
<212> TYPE: DNA
<213> ORGANISM: Artificial Sequence
<220> FEATURE:
<223> OTHER INFORMATION: Synthetic primer

<400> SEQUENCE: 11
catctactaa accaatcttc tatttctaac actaactaa        39

<210> SEQ ID NO 12
<211> LENGTH: 16
<212> TYPE: DNA
<213> ORGANISM: Artificial Sequence
<220> FEATURE:
<223> OTHER INFORMATION: Synthetic probe

<400> SEQUENCE: 12
aaacccgaat attcac        16

<210> SEQ ID NO 13
<211> LENGTH: 16
<212> TYPE: DNA
<213> ORGANISM: Artificial Sequence
<220> FEATURE:
<223> OTHER INFORMATION: Synthetic probe

<400> SEQUENCE: 13
aaacccaaat attcac        16

<210> SEQ ID NO 14
<211> LENGTH: 248
<212> TYPE: PRT
<213> ORGANISM: Homo sapiens

<400> SEQUENCE: 14

```
Met Ala Ala Gln Ser Ala Pro Lys Val Val Leu Lys Ser Thr Thr Lys
1               5                   10                  15

Met Ser Leu Asn Glu Arg Phe Thr Asn Met Leu Lys Asn Lys Gln Pro
            20                  25                  30

Thr Pro Val Asn Ile Arg Ala Ser Met Gln Gln Gln Gln Gln Leu Ala
        35                  40                  45

Ser Ala Arg Asn Arg Arg Leu Ala Gln Gln Met Glu Asn Arg Pro Ser
    50                  55                  60

Val Gln Ala Ala Leu Lys Leu Lys Gln Ser Leu Lys Gln Arg Leu Gly
65                  70                  75                  80

Lys Ser Asn Ile Gln Ala Arg Leu Gly Arg Pro Ile Gly Ala Leu Ala
                85                  90                  95

Arg Gly Ala Ile Gly Gly Arg Gly Leu Pro Ile Ile Gln Arg Gly Leu
            100                 105                 110

Pro Arg Gly Gly Leu Arg Gly Gly Arg Ala Thr Arg Thr Leu Leu Arg
        115                 120                 125

Gly Gly Met Ser Leu Arg Gly Gln Asn Leu Arg Gly Gly Arg Ala
    130                 135                 140

Val Ala Pro Arg Met Gly Leu Arg Arg Gly Val Arg Gly Arg Gly
145                 150                 155                 160
```

```
Gly Pro Gly Arg Gly Gly Leu Gly Arg Gly Ala Met Gly Arg Gly
            165                 170                 175

Ile Gly Gly Arg Gly Arg Gly Met Ile Gly Arg Gly Arg Gly Gly Phe
        180                 185                 190

Gly Gly Arg Gly Arg Gly Arg Gly Arg Gly Ala Leu Ala Arg
        195                 200                 205

Pro Val Leu Thr Lys Glu Gln Leu Asp Asn Gln Leu Asp Ala Tyr Met
    210                 215                 220

Ser Lys Thr Lys Gly His Leu Asp Ala Glu Leu Asp Ala Tyr Met Ala
225                 230                 235                 240

Gln Thr Asp Pro Glu Thr Asn Asp
            245

<210> SEQ ID NO 15
<211> LENGTH: 25
<212> TYPE: DNA
<213> ORGANISM: Artificial Sequence
<220> FEATURE:
<223> OTHER INFORMATION: Synthetic primer

<400> SEQUENCE: 15
tgttgagttt agaagttaag ttgga                                   25

<210> SEQ ID NO 16
<211> LENGTH: 22
<212> TYPE: DNA
<213> ORGANISM: Artificial Sequence
<220> FEATURE:
<223> OTHER INFORMATION: synthetic primer

<400> SEQUENCE: 16
acaatacccc taaaatacaa aa                                      22

<210> SEQ ID NO 17
<211> LENGTH: 24
<212> TYPE: DNA
<213> ORGANISM: Artificial Sequence
<220> FEATURE:
<223> OTHER INFORMATION: Synthetic primer

<400> SEQUENCE: 17
agaggtggta atttaggttt gtgt                                    24

<210> SEQ ID NO 18
<211> LENGTH: 24
<212> TYPE: DNA
<213> ORGANISM: Artificial Sequence
<220> FEATURE:
<223> OTHER INFORMATION: Synthetic primer

<400> SEQUENCE: 18
accatcacaa tttactcatc ctca                                    24

<210> SEQ ID NO 19
<211> LENGTH: 22
<212> TYPE: DNA
<213> ORGANISM: Artificial Sequence
<220> FEATURE:
<223> OTHER INFORMATION: Synthetic primer

<400> SEQUENCE: 19
ggttttgtgg gttggaagtt ag                                      22
```

```
<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20 accacccct ccttcaacta                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
atggttggag tagatgagat                                             20

<210> SEQ ID NO 22
<211> LENGTH: 20
<212> TYPE: DNA
<213> ORGANISM: Artificial Sequence
<220> FEATURE:
<223> OTHER INFORMATION: Synthetic primer

<400> SEQUENCE: 22
acaccactac actccaccct                                             20
```

DNA METHYLATION IN INFLAMMATORY DISEASE

CROSS REFERENCE TO RELATED APPLICATIONS

This application is a Continuation in Part of PCT/US2017/066708, filed on Dec. 15, 2017, which claims the benefit to U.S. Provisional Patent Application No. 62/436,137, filed on Dec. 19, 2016, each of which is hereby incorporated by reference in their entirety.

STATEMENT OF GOVERNMENT SUPPORT

This invention was made with government support under TR001108 and RR020128 awarded by the National Institutes of Health. The government has certain rights in the invention.

STATEMENT IN SUPPORT FOR FILING A SEQUENCE LISTING

A computer readable form of the Sequence Listing containing the file named "295533SeqList_ST25.txt", created on Jun. 17, 2019, which is 11 kilobytes in size (as measured in MICROSOFT WINDOWS® EXPLORER), is provided herein and is herein incorporated by reference.

BACKGROUND OF DISCLOSURE

Diabetes mellitus is a multifactorial disease, which occurs following the dysfunction or death of insulin-producing beta cells in the pancreas. Globally, there is an alarming increase in the incidence of type 1 diabetes (T1D) and type 2 diabetes (T2D), and it is estimated that currently 420 million individuals are affected both by T1D and T2D worldwide. In addition, the prevalence of diabetes is expected to increase by 50% over the next 10 years. Traditionally, both forms of diabetes have been viewed as distinct: T1D develops as a result of selective destruction of pancreatic 13 cells by the immune system, and T2D develops secondary to insufficient insulin secretion in the context of insulin resistance in peripheral tissues. In both forms, clinical manifestations of disease occur only after substantial $\beta$ cell loss, and application of therapeutic interventions at this time point have had only limited success in restoring of $\beta$-cell mass and function. Activation of stress pathways within the islets occurs during the very early phases of both T1D and T2M; therefore, detection of islet stress signals has the potential to serve as an early biomarker of future clinical disease.

During obesity, insulin resistance in the muscle, liver, and adipose tissue increases the demand for insulin secretion from the $\beta$ cell to maintain glucose homeostasis. The inability of the $\beta$ cell to fully compensate is a major factor in the progression from normoglycemia to dysglycemia and frank type 2 diabetes (T2D) in adults and youth. It has been known for over 60 years that $\beta$ cell mass is reduced in individuals with T2D compared to obese and lean non-diabetic controls, suggesting that reductions in $\beta$ cell mass might account for the loss of $\beta$ cell function. One hypothesis is that dynamic loss of $\beta$ cells with disease progression is the underlying cause. Studies from cadaveric donors suggest that $\beta$ cell apoptosis accounts for $\beta$ cell loss, whereas other findings in mice and humans suggest that dedifferentiation of $\beta$ cells may also be a key feature.

Recently, the measurement of circulating unmethylated DNA encoding preproinsulin (INS) has been proposed as a biomarker of islet $\beta$ cell damage and $\beta$ cell death. Particularly, it was previously shown that INS DNA in $\beta$ cells has a much higher frequency of unmethylated CpG sites compared to other cell types. Further, the relative abundance of unmethylated INS DNA in the circulation was shown to be elevated in both mice and humans with recent-onset T1D, and higher relative abundances correlated temporally to more active $\beta$ cell destruction.

$\beta$ cells and many other cell types in the islet contain some fraction of both unmethylated and methylated INS DNA. In a differentially methylated DNA (DMD) assay used to monitor 13 cell death in vivo, cell-free unmethylated CpG sites in preproinsulin (INS) DNA in circulation reflected DNA liberated from dying $\beta$ cells with methylated CpG sites in preproinsulin (INS) DNA in the circulation presumably representing DNA liberated from dying non-$\beta$ cells that had dedifferentiated. The loss of functional $\beta$ cell mass is believed to underlie virtually all forms of diabetes, but in T2D the primary etiology remains unclear. Accordingly, given the increased frequency of unmethylated INS CpG sites in insulin-producing beta cells, the ratio of unmethylated to methylated INS DNA released into the circulation upon cell death is considered a reflection of $\beta$-cell death.

Applicant has recently developed a multiplex PCR based assay using a more precise droplet digital PCR (ddPCR) technique to directly quantitate differentially methylated DNA (DMD) species. Using this technique applicant has discovered that subjects with new onset (T1D) display significantly elevated levels of both unmethylated and methylated INS DNA compared to controls (Fisher, et al. Diabetes 2015; 64:3867-72). Moreover, $\beta$ cells have been identified as a primary, but not exclusive, source of unmethylated INS DNA.

Accordingly, there is a need for biomarkers and diagnostic methods for evaluating biomarkers that are specific for inflammation and autoimmunity. The present disclosure is directed to methods of detecting and measuring the methylated state of cell free DNAs of an individual as a diagnostic or prognostic indicator of the health of a patient.

Sepsis represents another disease state that can be diagnosed by analysis of the methylated state of cell free DNAs of an individual. Sepsis is a potentially life-threatening complication of an infection. Sepsis occurs when chemicals released into the bloodstream to fight the infection trigger inflammatory responses throughout the body. This inflammation can trigger a cascade of changes that can damage multiple organ systems, causing them to fail. Diagnosis is based on sepsis-related organ failure assessment score (SOFA) to determine the extent of a patient's organ function or rate of failure. Scoring is based on six different scores for the respiratory, cardiovascular, hepatic, coagulation, renal and neurological systems. The quick SOFA score provides an initial way to identify patients at high risk for poor outcome with an infection. The qSOFA simplifies the SOFA score by only including its 3 clinical criteria and by including "any altered mentation". Early diagnosis is necessary for properly managing sepsis and to reduce mortality from severe sepsis. Detection of methylated cell free DNAs can be used to assist in the early diagnosis of sepsis and allow for early treatment.

SUMMARY

The present disclosure is generally related to evaluating circulating methylated and unmethylated DNA that are specific for inflammation. Accordingly, in one aspect, the present disclosure is directed to the use of a circulating unmethylated DNA, a circulating methylated DNA, and combinations thereof as a biomarker for systemic inflammation.

In another aspect, the present disclosure is directed to use of a circulating unmethylated DNA, a circulating methylated DNA, and combinations thereof as a biomarker for sepsis.

In another aspect, the present disclosure is directed to a method for detecting sepsis in a subject having, or suspected of having, sepsis. The method comprises: amplifying methylated preproinsulin DNA in a sample obtained from the subject; amplifying unmethylated preproinsulin DNA in the sample obtained from the subject; detecting whether a nucleotide from the preproinsulin transcriptional start site is methylated or unmethylated; comparing the concentration of methylated preproinsulin DNA and the concentration of unmethylated preproinsulin DNA from the subject to the concentration of methylated preproinsulin DNA and the concentration of unmethylated preproinsulin DNA from a subject not having, or not suspected of having, sepsis; and diagnosing the subject as being suspected of having sepsis if the concentration of methylated preproinsulin DNA from the subject are elevated when compared to the concentration of methylated preproinsulin DNA of the control.

Compared to healthy controls, applicants have discovered that levels of differentially methylated chromatin target of PRMT1 (CHTOP) and preproinsulin (INS) are higher in youth with new onset type 1 diabetes and in healthy youth who have first-degree relatives with type 1 diabetes. When tested in youth across a spectrum of metabolic dysfunction, increased levels of unmethylated INS and CHTOP were observed in obese individuals compared to lean controls. Together, these data indicate that simultaneous measurement of both INS and CHTOP will provide a more accurate assessment of β-cell death in patients with T1D and raise new questions about beta cell health in populations at risk for both T1D and T2D development. Accordingly the data presented herein supports the use of multiple parameters to increase the accuracy of biomarkers of beta cell health in youth with diabetes or at risk for developing diabetes.

In one embodiment the present disclosure relates to unmethylated and methylated DNA as biomarkers of an active inflammatory/autoimmune process. In one embodiment the present disclosure is directed to the detection and relative quantitation of the methylated state of preproinsulin (INS) DNA and chromatin target of PRMT1 (CHTOP) DNA in a patient's cell free circulating DNA. More particularly, the present disclosure relates to the detection of unmethylated and methylated preproinsulin (INS) DNA and chromatin target of PRMT1 (CHTOP) DNA as biomarkers of an active inflammatory/autoimmune process and/or sepsis.

In one embodiment a kit is provided for quantitating unmethylated and methylated concentrations of preproinsulin (INS) DNA and chromatin target of PRMT1 (CHTOP) DNA sequences in a sample. In one embodiment the kit for measuring the methylated state of preproinsulin and CHTOP comprises a nucleic acid molecule selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8; SEQ ID NO: 10, SEQ ID NO: 11, SEQ ID NO: 12 and SEQ ID NO: 13. In one embodiment the kit for measuring the methylated state of preproinsulin and CHTOP comprises a nucleic acid molecule selected from the group consisting of SEQ ID NO: 3, SEQ ID NO: 4, SEQ ID NO: 7, SEQ ID NO: 8; SEQ ID NO: 12 and SEQ ID NO: 13. In one embodiment the nucleic acid molecules of the kit are labeled with a detectable marker, including for example a radioisotope or a fluorophore. In one embodiment the kit comprises the nucleotide sequence of SEQ ID NO: 4 and SEQ ID NO: 13.

BRIEF DESCRIPTION OF THE DRAWINGS

The disclosure will be better understood, and features, aspects and advantages other than those set forth above will become apparent when consideration is given to the following detailed description thereof, such detailed description makes reference to the following drawings, wherein:

FIGS. 1A-1D: FIGS. 1A and 1B depict mouse DMD assay specificity and validation. FIG. 1A depicts two-dimensional plots using plasmid standards for unmethylated and methylated mouse Ins2 DNA and for a 1:1 mixture of the two plasmids. Arrows identify the unmethylated, methylated, and unmethylated+methylated (double-positive) Ins2 DNA-containing droplets. FIG. 1B depicts quantitation of plasmid dilution curves, presented as copies/µl. FIGS. 1C and 1D depict quantitation of dilution curves of serum spiked with mouse DNA for unmethylated Ins2 DNA (FIG. 1C) and methylated Ins2 DNA (FIG. 1D). $R^2$=0.9733 for unmethylated Ins2 DNA and $R^2$=0.9917 for methylated Ins2 DNA.

FIG. 2A depicts body weight measurements of C57BL/6J mice fed a low fat diet (LFD) or high fat diet (HFD) and treated with STZ to induce β cell death. N=6-12 mice total for each of 4 groups, done on two separate occasions. Data are presented as mean±SEM; *$P<0.05$ compared to LFD. #$P<0.05$ compared to no-STZ.

FIG. 2B depicts fasting blood glucose measurements of C57BL/6J mice fed a low fat diet (LFD) or high fat diet (HFD) and treated with STZ to induce β cell death. N=6-12 mice total for each of 4 groups, done on two separate occasions. Data are presented as mean±SEM; *$P<0.05$ compared to LFD. #$P<0.05$ compared to no-STZ.

FIG. 2C depicts area under the curve of intraperitoneal glucose tolerance tests of C57BL/6J mice fed a low fat diet (LFD) or high fat diet (HFD) and treated with STZ to induce 13 cell death. N=6-12 mice total for each of 4 groups, done on two separate occasions. Data are presented as mean±SEM; *$P<0.05$ compared to LFD. #$P<0.05$ compared to no-STZ.

FIG. 2D depicts β cell mass of C57BL/6J mice fed a low fat diet (LFD) or high fat diet (HFD) and treated with STZ to induce β cell death. N=6-12 mice total for each of 4 groups, done on two separate occasions. Data are presented as mean±SEM; *$P<0.05$ compared to LFD. #$P<0.05$ compared to no-STZ.

FIG. 9A presents data for unmethylated CHTOP DNA; FIG. 9B presents data for methylated CHTOP DNA; FIG. 9C presents data for unmethylated INS DNA; and FIG. 9D presents data for methylated INS DNA. Data are presented as mean±SEM. *P<0.05 for the comparisons indicated.

Figure 1C:
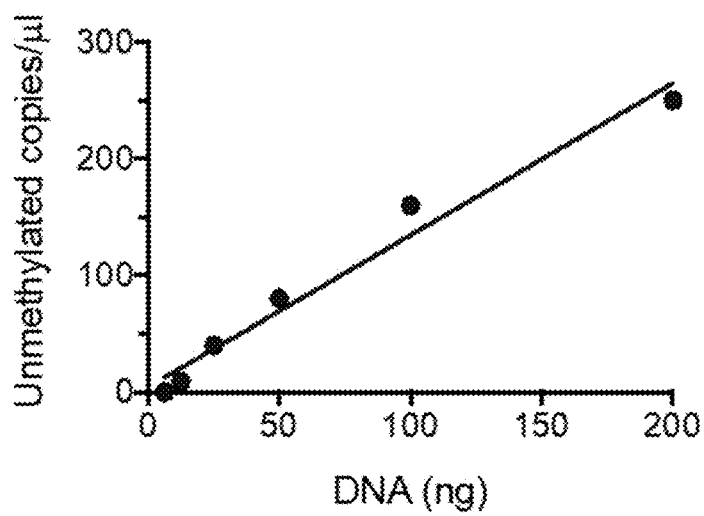

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the scope of the disclosure as defined by the appended claims.

DETAILED DESCRIPTION

Definitions

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure reference to "diabetes" without a further designation encompasses both type 1 and type 2 diabetes.

As used herein, "a subject in need thereof" (also used interchangeably herein with "a patient in need thereof") refers to a subject susceptible to, or at risk of, a specified disease, disorder, or condition. The methods of screening circulating methylated and unmethylated DNA can be used with a subset of subjects who are susceptible to or at elevated risk of systemic inflammation. The methods of screening circulating methylated and unmethylated DNA can be used with a subset of subjects who are susceptible to or at elevated risk of sepsis. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

As used herein, "susceptible" and "at risk" refer to having little resistance to a certain disease, disorder or condition, including being genetically predisposed, having a family history of, and/or having symptoms of the disease, disorder or condition.

As used herein, the term "treating" includes alleviating the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

As used herein the term "body fluid" includes any fluid or fluid secretion (such as blood, lymph, saliva, semen, or urine) of the body.

Embodiments

In accordance with one embodiment the methylated state of cell free DNAs in a patient's body fluids, including for example plasma or sera, is determined as a measurement of the health of the patient and/or detection of an inflammatory disease. More particularly, in one embodiment the simultaneous measurement of the methylated state of both INS and CHTOP is used as a measurement of the health of the patient and to detect or predict the presence of a disease state or condition. In one embodiment the simultaneous detection of unmethylated DNAs of INS and CHTOP specific DNA's in cell free DNA of the patient can be used to detect β-cell death and serve as an indicator of an inflammatory disease, early development of T1D or sepsis.

In accordance with one embodiment a method for assessing the heath of a patient's β-cell population is provided by detecting the presence of cell free β-cell specific DNAs in a patient's body fluids. In accordance with one embodiment islet β-cell death can be detected, and used to diagnose early stage diabetes or inflammatory disease, by detecting unmethylated sequences of the preproinsulin (INS) or CHTOP gene.

In accordance with one embodiment a method for determining the methylated state of human preproinsulin and human chromatin target of PRMT1 (CHTOP) and/or preproinsulin (INS) DNA in a patient's cell free circulating DNA is provided, wherein the methylation state of preproinsulin and/or chromatin target of PRMT1 (CHTOP) DNA is determined using standard techniques. In one embodiment the method comprises the steps of subjecting a DNA sample, isolated from a plasma or serum sample recovered from a patient, to a bisulfite reaction, and analyzing the bisulfite treated DNA. In one embodiment the methylated state is determined using mass spectrometer analysis or use of nucleic acid probes specific for a methylated vs unmethylated sequence associated with CHTOP and/or preproinsulin DNA. In one embodiment the methylated state of both CHTOP and INS is determined for the DNA isolated from the same patient sample, including isolated cell free DNAs of a patient. In one embodiment at least two genes of the DNA sample are amplified using standard PCR techniques, optionally prior to the step of conducting the bisulfite reaction.

In one embodiment a method for determining the methylated state of human preproinsulin and human chromatin target of PRMT1 (CHTOP) DNA in a patient's cell free circulating DNA is provided, wherein the method comprises the steps of subjecting a DNA sample isolated from a plasma or serum sample recovered from said patient to a PCR amplification step wherein the amplification is conducted using PCR primers specific for a sequence that comprises a differentially methylated nucleotide. In one embodiment the method comprises the steps of amplifying unmethylated CHTOP and/or preproinsulin DNA in a sample obtained from a patient, and optionally amplifying methylated CHTOP and/or preproinsulin DNA in a sample. In one embodiment the sample is obtained from a subject suspected of having sepsis. In one embodiment both the unmethylated CHTOP and/or preproinsulin DNA and the methylated CHTOP and/or preproinsulin DNA are amplified and a comparison is made between a) the concentration of methylated preproinsulin DNA and unmethylated preproinsulin DNA in the sample with the concentration of methylated preproinsulin DNA and unmethylated preproinsulin DNA in a control; or b) a comparison is made between the concentration of methylated CHTOP DNA and unmethylated CHTOP DNA in the sample with the concentration of methylated CHTOP DNA and unmethylated CHTOP DNA in a control; or c) b) a comparison is made between the concentration of methylated CHTOP and preproinsulin DNA and unmethylated CHTOP and preproinsulin DNA in the sample with the concentration of methylated CHTOP and preproinsulin DNA and unmethylated CHTOP and preproinsulin DNA in a control.

In one embodiment the cell free DNA of a patient is analyzed to detect the presence of unmethylated DNAs of the CHTOP gene sequence. In particular, differentially methylated sites of the CHTOP gene sequence are analyzed to determine if the differentially methylated site is unmethylated. In one embodiment an individual cell free sample of DNA isolated from a patient is analyzed for the presence of both CHTOP and preproinsulin (INS) DNA that is unmethylated at one or more differentially methylated sites of the gene sequence. In one embodiment, the differentially methylated site of the respective genes is the nucleotide located at position −69 from the human preproinsulin (INS) transcriptional start site and the CpG site of Chr1:153610817 of the CHTOP gene.

In one embodiment a method for detecting CHTOP and preproinsulin (INS) DNA that is unmethylated at the CpG site of Chr1:153610817 of the CHTOP gene and at position −69 from the human preproinsulin (INS) transcriptional start site comprises the steps of subjecting a patient's cell free DNA sample to a bisulfite reaction and then contacting the DNA sample d with a nucleic acid probe comprising the sequence of AAACCCAAATATTCAC (SEQ ID NO: 13) and a probe comprising the sequence ACCCCTACCACCTAAC (SEQ ID NO: 4).

In accordance with one embodiment the detection of circulating unmethylated DNA, a circulating methylated DNA, and combinations thereof is used as a biomarker for inflammation. In one embodiment the detected circulating DNA is DNA encoding the CHTOP and/or preproinsulin DNA. In a further embodiment the methylated state of both the preproinsulin and CHTOP DNA are analyzed in a sample of cell free DNA isolated from a patient.

Methods for Diagnosing systemic inflammation using circulating unmethylated DNA and methylated DNA In one aspect, the present disclosure is directed to use of a circulating unmethylated DNA, a circulating methylated DNA, and combinations thereof as a biomarker for systemic inflammation. The method includes amplifying methylated preproinsulin (INS) DNA and/or chromatin target of PRMT1 (CHTOP) DNA in a sample obtained from the subject; amplifying unmethylated preproinsulin DNA and/or chromatin target of PRMT1 (CHTOP) DNA; detecting whether a nucleotide of the preproinsulin DNA and/or chromatin target of PRMT1 (CHTOP) DNA is methylated or unmethylated; comparing the concentration of methylated preproinsulin and/or CHTOP DNA and unmethylated preproinsulin and/or CHTOP DNA in the sample with the concentration of methylated preproinsulin and/or (CHTOP) DNA and unmethylated preproinsulin and/or CHTOP DNA in a control subject; and determining that the subject has systemic inflammation when the concentration of methylated preproinsulin and/or CHTOP DNA in the sample is greater than the concentration of methylated preproinsulin and/or CHTOP DNA in the control subject. In one embodiment the sample is recovered from a patient suspected of having sepsis and the method is used for early diagnosis of sepsis.

In accordance with one embodiment a method of treating a patient suffering from inflammation is provided. The method comprises measuring the concentration of methylated preproinsulin and/or CHTOP DNA in a cell free sample of DNA isolated from a patient, wherein an elevated concentration of methylated preproinsulin and/or CHTOP DNA in the sample relative to the concentration of methylated preproinsulin and/or CHTOP DNA in a cell free sample of DNA isolated from a control subject is indicative of an inflammatory condition in the patient; and treating the patient with an acceptable pharmaceutical composition. Suitable pharmaceutical compositions comprise anti-inflammatory pain reliever drugs (e.g., nonsteroidal anti-inflammatory drugs such as aspirin, ibuprofen, or Celebrex) or corticosteroids (such as prednisone) or immune-suppressant drugs.

In one embodiment, suitable methylated and unmethylated DNA includes methylated and unmethylated human CHTOP, methylated and unmethylated human preproinsulin (INS) DNA and methylated and unmethylated mouse preproinsulin (Ins2) DNA. In particular, a nucleotide located at position −69 from the transcriptional start site of the human INS DNA is analyzed. In another embodiment, a nucleotide located at position −182 from the transcriptional start site of the mouse Ins2 DNA is analyzed. A particularly suitable reference sequence for identifying position −69 of the human INS DNA can be found in the preproinsulin gene provided by GenBank Accession number V00565 (GI: 33930; Ensembl number: ENSG00000254647; provided herein as SEQ ID NO: 9).

A particularly suitable reference sequence for identifying position −182 of the mouse Ins2 DNA can be found in the mouse preproinsulin (Ins2) gene provided by GeneID: 16334.

In one embodiment suitable methylated and unmethylated DNA includes methylated and unmethylated human chromatin target of PRMT1 (CHTOP). In particular, a nucleotide located at the CpG site of Chr1:153610817 of the CHTOP gene is analyzed.

Suitable amplification methods are known to those skilled in the art such as, for example, polymerase chain reaction and isothermal amplification methods. Suitable polymerase chain reaction methods for amplifying preproinsulin (human INS and mouse Ins2) DNA and CHTOP DNA are known to those skilled in the art. A particularly suitable amplification method includes DROPLET DIGITAL™ PCR (ddPCR™). ddPCR™ technology employs the analysis of discrete individual PCR reactions (up to 20,000/sample) to identify the absence or presence of the target DNA, and subsequently utilizes Poisson statistics to extrapolate the number of copies of the target DNA in the sample.

In one aspect, the nucleotide located at position −69 from the human preproinsulin (INS) transcriptional start site is cytosine. In one aspect, the nucleotide located at position −182 from the mouse preproinsulin (Ins2) transcriptional start site is cytosine.

In one aspect, the method includes amplifying the methylated preproinsulin DNA in the sample using an oligonucleotide comprising SEQ ID NO: 3. In another aspect, the method includes amplifying the unmethylated preproinsulin DNA in the sample using an oligonucleotide comprising SEQ ID NO: 4. In another aspect, the methylated preproinsulin DNA in the sample the unmethylated preproinsulin DNA in the sample is amplified using a primer pair, wherein the primer pair includes an oligonucleotide comprising SEQ ID NO: 3 and an oligonucleotide comprising SEQ ID NO: 4.

In another aspect, the method further includes amplifying the preproinsulin (INS) promoter. The preproinsulin promoter can be amplified using a first oligonucleotide comprising SEQ ID NO: 1 and a second oligonucleotide comprising SEQ ID NO: 2.

In another aspect, the method further includes determining the concentration of methylated preproinsulin DNA. The methylated human preproinsulin DNA is methylated at a nucleotide located at position −69 from the human preproinsulin transcriptional start site. The nucleotide located at position −69 from the human preproinsulin transcriptional start site is cytosine. The methylated mouse preproinsulin DNA is methylated at a nucleotide located at position −182 from the mouse preproinsulin transcriptional start site. The nucleotide located at position −182 from the mouse preproinsulin transcriptional start site is cytosine. As described herein, statistics such as, for example, Poisson statistics, can be used to extrapolate the number of copies, and thus, the concentration of the methylated and unmethylated preproinsulin DNA and/or chromatin target of PRMT1 (CHTOP) DNA in the sample.

In another aspect, the method further includes determining the concentration of unmethylated preproinsulin DNA. The unmethylated human preproinsulin DNA is methylated at a nucleotide located at position −69 from the human preproinsulin transcriptional start site. The nucleotide located at position −69 from the human preproinsulin transcriptional start site is cytosine. The unmethylated mouse preproinsulin DNA is methylated at a nucleotide located at position −182 from the mouse preproinsulin transcriptional start site. The nucleotide located at position −182 from the mouse preproinsulin transcriptional start site is cytosine.

In one aspect, the method includes amplifying the methylated CHTOP DNA in the sample using an oligonucleotide comprising SEQ ID NO: 10. In another aspect, the method includes amplifying the unmethylated CHTOP DNA in the sample using an oligonucleotide comprising SEQ ID NO: 11. The second PCR primer can be selected from any region of the CHTOP DNA and can be the same for both amplification of the methylated and unmethylated versions of the CHTOP DNA.

In another aspect, the method includes subjecting (i.e., treating) the preproinsulin and/or CHTOP DNA in the sample to a bisulfite reaction. The preproinsulin and/or CHTOP DNA can suitably be treated alone after isolation and purification from the sample or the preproinsulin and/or CHTOP DNA can suitably be treated with all (the total) or part of the DNA in the sample. The preproinsulin and/or CHTOP DNA is subjected to a bisulfite reaction by treating the preproinsulin and/or CHTOP DNA, the part of the DNA, and/or the total DNA with bisulfite. The bisulfite treatment can be performed using standard methods such as, for example, EZ DNA METHYLATION™ kit (commercially available from Zymo Research, Irvine, Calif.) and EZ DNA METHYLATION-LIGHTNING Kit (commercially available from Zymo Research, Irvine, Calif.). Treatment of DNA with bisulfite results in the conversion of unmethylated cytosines to uracils.

In another aspect, the copy number per microliter of methylated preproinsulin and/or CHTOP DNA and the copy number per microliter of unmethylated preproinsulin and/or CHTOP DNA are calculated.

Suitable samples can be serum, plasma, whole blood and urine. Particularly suitable samples include serum, plasma and urine. Total DNA and preproinsulin DNA can be extracted from serum and plasma using standard methods such as, for example, ZR SERUM DNA Kit™ (commercially available from Zymo Research, Irvine, Calif.) and QIAamp DNA blood mini kit (commercially available from QIAGEN, Germantown, Md.). Preproinsulin (INS) DNA can be extracted from urine using standard methods such as, for example, ZR URINE DNA Kit™ (commercially available from Zymo Research, Irvine, Calif.), for example.

The concentration of methylated DNA and unmethylated DNA can be determined by measuring fluorescence. The concentration of methylated preproinsulin and/or CHTOP DNA and unmethylated preproinsulin and/or CHTOP DNA can be determined by measuring fluorescence. Fluorescence can be measured at 518 nm, 548 nm, and 582.

Suitable control subjects include, for example, a healthy adult subject, a healthy pediatric subject, a subject having type 1 diabetes for at least 8 weeks, a subject having type 1 diabetes for at least one year, an adult with obesity, an adult having type 2 diabetes, an adult having auto-immune hepatitis, and combinations thereof.

Methods for Diagnosing Sepsis in a Subject

In another aspect, the present disclosure is directed to a method for diagnosing sepsis in a subject suspected of having sepsis. The method includes amplifying methylated preproinsulin DNA in a sample obtained from the subject suspected of having sepsis; amplifying unmethylated preproinsulin DNA in the sample obtained from the subject suspected of having sepsis; detecting whether a nucleotide is methylated or unmethylated; comparing the concentration of methylated preproinsulin DNA and unmethylated preproinsulin DNA in the sample with the concentration of methylated preproinsulin DNA and unmethylated preproinsulin DNA in a control subject; and determining that the subject has sepsis when the concentration of methylated preproinsulin DNA in the sample is greater than the concentration of methylated preproinsulin DNA in the control subject. Upon detection of a patient suffering for sepsis, the patient can be treated with combinations of intravenous antibiotics to treating the cause of the sepsis.

In one aspect, the detected DNA sequences comprise a nucleotide located at position −69 from the human preproinsulin (INS) transcriptional start site that is cytosine. In one aspect, the nucleotide located at position −182 from the mouse preproinsulin (Ins2) transcriptional start site is cytosine.

A particularly suitable reference sequence for identifying position −69 from the human preproinsulin (INS) transcriptional start site can be found in the preproinsulin gene having the GenBank Accession number V00565 (GI:33930; Ensembl number: ENSG00000254647; provided herein as SEQ ID NO:9).

A particularly suitable reference sequence for identifying position −182 from the mouse preproinsulin (Ins2) transcriptional start site can be found in the mouse preproinsulin (Ins2) gene having the GeneID: 16334.

Suitable amplification methods are known to those skilled in the art such as, for example, polymerase chain reaction and isothermal amplification methods. Suitable polymerase chain reaction methods for amplifying preproinsulin (human INS and mouse Ins2) DNA are known to those skilled in the art. A particularly suitable amplification method is DROPLET DIGITAL™ PCR (ddPCR™). ddPCR™ technology employs the analysis of discrete individual PCR reactions (up to 20,000/sample) to identify the absence or presence of the target DNA, and subsequently utilizes Poisson statistics to extrapolate the number of copies of the target DNA in the sample.

In one aspect, the nucleotide located at position −69 from the human preproinsulin (INS) transcriptional start site is cytosine. In one aspect, the nucleotide located at position −182 from the mouse preproinsulin (Ins2) transcriptional start site is cytosine.

In one aspect, the method includes amplifying the methylated preproinsulin DNA in the sample using an oligonucleotide comprising SEQ ID NO: 3. In another aspect, the method includes amplifying the unmethylated preproinsulin DNA in the sample using an oligonucleotide comprising SEQ ID NO: 4. In another aspect, the methylated preproinsulin DNA in the sample the unmethylated preproinsulin DNA in the sample is amplified using a primer pair, wherein the primer pair includes an oligonucleotide comprising SEQ ID NO: 3 and an oligonucleotide comprising SEQ ID NO: 4.

In another aspect, the method further includes amplifying the preproinsulin promoter. The preproinsulin promoter can be amplified using a first oligonucleotide comprising SEQ ID NO: 1 and a second oligonucleotide comprising SEQ ID NO: 2.

In another aspect, the method further includes determining the concentration of methylated preproinsulin DNA. The methylated human preproinsulin DNA is methylated at a nucleotide located at position −69 from the human preproinsulin transcriptional start site. The nucleotide located at position −69 from the human preproinsulin transcriptional start site is cytosine. The methylated mouse preproinsulin DNA is methylated at a nucleotide located at position −182 from the mouse preproinsulin transcriptional start site. The nucleotide located at position −182 from the mouse preproinsulin transcriptional start site is cytosine. As described herein, statistics such as, for example, Poisson statistics, can be used to extrapolate the number of copies, and thus, the concentration of the methylated and unmethylated preproinsulin DNA in the sample.

In another aspect, the method further includes determining the concentration of unmethylated preproinsulin DNA. The unmethylated human preproinsulin (INS) DNA is methylated at a nucleotide located at position −69 from the preproinsulin (INS) transcriptional start site. The nucleotide located at position −69 from the human preproinsulin (INS) transcriptional start site is cytosine. The unmethylated mouse preproinsulin (Ins2) DNA is methylated at a nucleotide located at position −182 from the preproinsulin (Ins2) transcriptional start site. The nucleotide located at position −182 from the mouse preproinsulin (Ins2) transcriptional start site is cytosine.

In another aspect, the method includes subjecting (i.e., treating) the preproinsulin DNA in the sample to a bisulfite reaction. The preproinsulin DNA can suitably be treated alone after isolation and purification from the sample and the preproinsulin DNA can suitably be treated with all (the total) or part of the DNA in the sample. The preproinsulin DNA is subjected to a bisulfite reaction by treating the preproinsulin DNA and/or the total DNA with bisulfite. The bisulfite treatment can be performed using standard methods such as, for example, EZ DNA METHYLATION™ kit (commercially available from Zymo Research, Irvine, Calif.) and EZ DNA METHYLATION-LIGHTNING Kit (commercially available from Zymo Research, Irvine, Calif.). Treatment of DNA with bisulfite results in the conversion of unmethylated cytosines to uracils.

In another aspect, the copy number per microliter of methylated preproinsulin DNA and the copy number per microliter of unmethylated preproinsulin DNA are determined.

Suitable samples can be serum, plasma, whole blood and urine. Particularly suitable samples include serum, plasma and urine. Total DNA and preproinsulin DNA can be extracted from serum and plasma using standard methods such as, for example, ZR SERUM DNA Kit™ (commercially available from Zymo Research, Irvine, Calif.) and QIAamp DNA blood mini kit (commercially available from QIAGEN, Germantown, Md.). Preproinsulin DNA can be extracted from urine using standard methods such as, for example, ZR URINE DNA Kit™ (commercially available from Zymo Research, Irvine, Calif.), for example.

The concentration of methylated DNA and unmethylated DNA can be determined by measuring fluorescence. The concentration of methylated preproinsulin DNA and unmethylated preproinsulin DNA can be determined by measuring fluorescence, for example by the use of fluorescent labeled probes specific for methylated or unmethylated DNAs. Methylated DNA specific probes include SEQ ID NO: SEQ ID NO: 3, SEQ ID NO: 7 and SEQ ID NO: 13. Unmethylated DNA specific probes include SEQ ID NO: 4, SEQ ID NO: 8 and SEQ ID NO: 13 Fluorescence can be measured at 518 nm, 548 nm, and 582.

Suitable control subjects include, for example, a healthy pediatric subject, a subject having type 1 diabetes for at least 8 weeks, a subject having type 1 diabetes for at least one year, a healthy adult subject, an adult with obesity, an adult having type 2 diabetes, an adult having auto-immune hepatitis, and combinations thereof.

In one embodiment the present disclosure is directed to the use of a circulating unmethylated DNA, a circulating methylated DNA, and combinations thereof as a biomarker for inflammation or sepsis. In one embodiment the methylated state of both the preproinsulin and CHTOP DNA are analyzed in a sample of cell free DNA isolated from a patient.

In one embodiment a method for determining inflammation in a subject suspected of having inflammation is provided wherein the method comprises:

amplifying methylated preproinsulin DNA in a sample obtained from the subject suspected of having inflammation;
amplifying unmethylated preproinsulin DNA in a sample obtained from the subject suspected of having inflammation;
comparing the concentration of methylated preproinsulin DNA and unmethylated preproinsulin DNA in the sample with the concentration of methylated preproinsulin DNA and unmethylated preproinsulin DNA in a control; and
determining that the subject has inflammation when the concentration of methylated preproinsulin DNA in the sample is greater than the concentration of methylated preproinsulin DNA in the control. In one embodiment the method further comprises analyzing whether a nucleotide located at position −69 from the human preproinsulin (INS) transcriptional start site is methylated or unmethylated. In one embodiment the method further comprises the steps of amplifying methylated CHTOP DNA in the sample obtained from the subject suspected of having inflammation; amplifying unmethylated CHTOP DNA in the sample obtained from the subject suspected of having inflammation; and comparing the concentration of methylated CHTOP DNA and unmethylated CHTOP DNA in the sample with the concentration of methylated CHTOP DNA and unmethylated CHTOP DNA in a control. In one embodiment preproinsulin DNA and/or CHTOP DNA in the sample is subjected to a bisulfite reaction either before or after the amplification step, typically after the amplification step. In one embodiment the sample is selected from the group consisting of serum, plasma, whole blood, and urine.

In one embodiment a method for determining sepsis in a subject suspected of having sepsis is provided wherein the method comprises:

amplifying methylated preproinsulin DNA in a sample obtained from the subject suspected of having sepsis;
amplifying unmethylated preproinsulin DNA in a sample obtained from the subject suspected of having sepsis;
comparing the concentration of methylated preproinsulin DNA and unmethylated preproinsulin DNA in the sample with the concentration of methylated preproinsulin DNA and unmethylated preproinsulin DNA in a control; and
determining that the subject has sepsis when the concentration of methylated preproinsulin DNA in the sample is greater than the concentration of methylated preproinsulin DNA in the control. In one embodiment the method further comprises analyzing whether a nucleotide located at position −69 from the human preproinsulin (INS) transcriptional start site is methylated or unmethylated. In one embodiment the method further comprises the steps of amplifying methylated CHTOP DNA in the sample obtained from the subject suspected of having sepsis; amplifying unmethylated CHTOP DNA in the sample obtained from the subject suspected of having sepsis; and comparing the concentration of methylated CHTOP DNA and unmethylated CHTOP DNA in the sample with the concentration of methylated CHTOP DNA and unmethylated CHTOP DNA in a control. In one embodiment the preproinsulin DNA and/or CHTOP DNA in the sample is subjected to a bisulfite reaction either before or after the amplification step, typically after the amplification step. In one embodiment the sample is selected from the group consisting of serum, plasma, whole blood, and urine.

Various functions and advantages of these and other embodiments of the present disclosure will be more fully understood from the examples described below. The following examples are intended to illustrate the benefits of the present disclosure, but do not exemplify the full scope of the disclosure.

EXAMPLES

Materials and Methods

Human Subjects

Serum samples were obtained from male and female adult subjects 18-65 years of age.

After an overnight fast, subjects underwent an oral glucose tolerance test (OGTT) with 75 g glucose. Subjects were divided into three categories based on OGTT 2 hr-glucose concentrations: normal glucose tolerance (controls, <140 mg/dL), impaired glucose tolerance (IGT; 140-199 mg/dL), and T2D (>200 mg/dL). Exclusion criteria included: Metformin use 4 weeks previous, thiazolidinediones use 6 months previous, T1D, other diabetes, pregnancy, weight fluctuation 6 months previous, current or past tobacco use, acute or chronic illness, pulmonary disease, or use of antidepressants. Serum samples were collected from male and female 6-20 years of age enrolled at Riley Children's Hospital with no disease history (controls), active inflammatory bowel disease (IBD) or acute sepsis. Participants were provided written informed consent for screening and study participation. The study was approved by the Indiana University School of Medicine Institutional Review Board.

Frozen serum samples from 150 youth ages 10 to <20 years old (Table 2) who participated in NIH-funded K24 grant of "Childhood Insulin Resistance" were used in the present analysis. A 2-hr OGTT was performed in obese participants as described before. GAD 65 kDa autoantibody and insulinoma-associated protein 2 autoantibody (IA2) were measured using the NIDDK standardized assay protocol as described before. Participants with diabetes were on either lifestyle-only, or metformin or metformin plus insulin.

Human Islet and Cell Line

Human islets were obtained from the Integrated Islet Distribution Program (IIDP). βH1 cells and human islets were incubated with cytokines (50 U/ml IL-1β and 1000 U/ml IFN-γ) for 0, 24, or 72 hours. Following incubation, DNA was extracted from both the cells and the supernatant.

Animals

Male C57BL/6J mice, C57BL/KsJ-db/db, and C57BL/KsJ-db/+ mice were obtained from the Jackson Laboratories and maintained under protocols approved by the Indiana University School of Medicine Institutional Animal Care and Use Committee or by the Lilly Research Labs Institutional Animal Care and Use Committee. C57BL/6J mice were acclimated for 1 week prior to being placed on either a low fat diet (10% kcal from fat, Research Diets; D12450B) or high fat diet (60% kcal from fat; Research Diets; D12492) starting at 8 weeks of age. C57BL/KsJ-db/db, and C57BL/KsJ-db/+ mice were feed a regular chow diet (Research Diets; 5008). Blood was harvested from the tail vein and processed as serum for the DMD assay. All mice were monitored for body weight and random blood glucose weekly. C57BL/6J mice underwent a glucose tolerance test using 2 g/kg lean mass after an overnight fast. A subset of C57BL/6J mice from each group was euthanized biweekly and pancreata were harvested for β cell mass measurements. After 10 weeks of diet treatment, a subset of C57BL6/J mice received streptozocin (STZ) at 55 mg/kg body weight daily for 5 days.

DNA Extraction and Bisulfite Treatment

DNA was isolated from 20-50 µl of serum or cellular supernatant using QIAamp DNA Blood Mini Kit (Qiagen) with 5 µg poly-A as a carrier. Cellular DNA was isolated using GenElute Mammalian Genomic DNA Miniprep Kit (Sigma-Aldrich). All samples then underwent bisulfite conversion using the EZ DNA Methylation kit or the EZ DNA Methylation-Lightning kit (Zymo Research), and conversion was verified using a pre- and postconversion sample in the ddPCR.

DMD Assay

Primers and dual-fluorescent probes for interrogating methylation at CpG position −69 at the human INS gene and at position −182 at the mouse Ins2 gene were described in Fisher et al. and (Diabetes 2015; 64(11):3867-3872) and Fisher et al. (Endocrinology 2013; 154(9):3476-3481). The DMD assay using droplet digital PCR (ddPCR) using primers and probes for mouse Ins2 and human INS were described in Fisher et al. and (Diabetes 2015; 64(11):3867-3872).

PCR Analysis

Each sample was analyzed by ddPCR utilizing a custom designed dual fluorescent probe-based multiplex assay. For amplification of the human INS promoter, the following primers were used: 5'-GGAAATTGTAGTTTTAGTTTT-TAGTTATTTGT-3' (forward) (SEQ ID NO: 1); 5'-AAAACCCATCTCCCCTACCTATCA-3' (reverse) (SEQ ID NO: 2) in combination with the following probes that detected methylation or unmethylation at position −69 relative to the transcriptional start site: 5'-ACCCC-TACCGCCTAAC-3' (VIC)—methylated (SEQ ID NO: 3); 5'-ACCCCTACCACCTAAC-3' (FAM)—unmethylated (SEQ ID NO: 4). Primers and probes for mouse Ins2 DNA are as follows: primers used included 5'-AATTGGTTTATT-AGGTTATTAGGGTTTTTTGTTAAGATTTTA-3' (forward) (SEQ ID NO: 5); 5'-ACTAAAACTACAATTTC-CAAACACTTCCCTAA-3' (reverse) (SEQ ID NO: 6); probes used included: 5'-CTCATTAAACGTCAACACC-3' (VIC) (SEQ ID NO: 7); 5'-CTCATTAAACATCAACACC-3' (FAM) (SEQ ID NO: 8).

The PCR was performed using ddPCR Supermix for Probes (No dUTP) (Bio-Rad Laboratories, Inc., Hercules, Calif.) with the following cycling conditions: 95° C. for 10 minutes, 94° C. for 30 seconds, 57.5° C. for 60 seconds for 40 amplification cycles. Droplets were analyzed by the QX200 Droplet Reader and QuantaSoft Software (Bio-Rad Laboratories, Inc., Hercules, Calif.), from which an absolute concentration (copies/µl) of methylated and unmethylated INS DNA was obtained in each subject's sample. This final concentration was extrapolated to copies of unmethylated or methylated INS DNA/µl serum, then log-transformed for parametric statistical analysis.

Morphometric Assessment of β Cell Mass

Pancreata from at least three different mice per group were fixed in 4% paraformaldehyde, paraffin embedded, and sectioned onto glass slides. The β cell mass was calculated as described in Maier et al. (J. Clin. Invest. 2010; 12(6):2156-2170).

Statistical Analysis

All data are presented as mean±SEM. For comparisons of methylated and unmethylated mouse Ins2 DNA levels, a two-tailed unpaired Student's t test was used. For analysis of methylated and unmethylated INS DNA levels, a Kruskal-Wallis (non-parametric) test was employed followed by a Dunnett's post-test (to compare values to healthy controls). Statistical significance was determined at $P<0.05$.

Example 1

In this Example, β cell death in mouse models of obesity and T2D was determined.

Figure 1D:
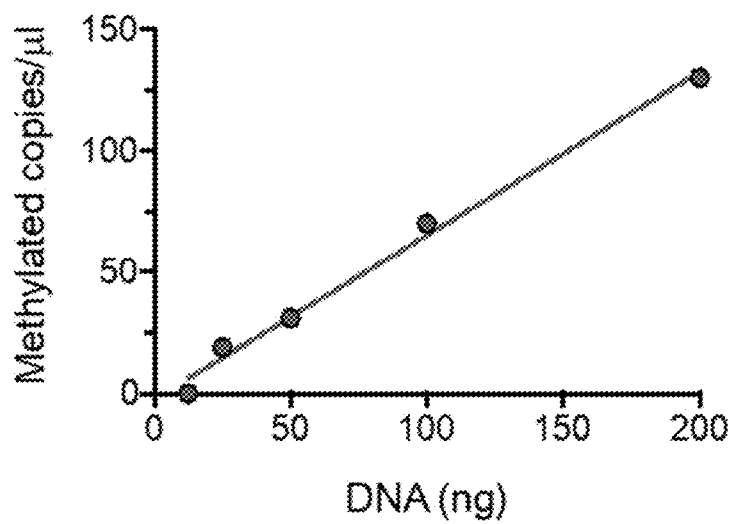

To assess β cell death in mouse models of obesity and T2D, the established real-time PCR-based DMD assay (described in Fisher et al., Endocrinology. 2013 September; 154(9):3476-81) was modified for compatibility with the more sensitive and specific ddPCR technique that allows for absolute quantitation of DNA copy numbers. The primers described in that study interrogated differential methylation at cytosine at position −182 bp (relative to the transcriptional start site) of the mouse Ins2 gene. The specificity of the primers in ddPCR was validated using plasmids containing cloned methylated or unmethylated Ins2 gene. As shown in the 2-dimensional ddPCR plots in FIG. 1A, the primers quantitatively distinguished mixtures of these plasmids. FIGS. 1B-1D show that the primers linearly and quantitatively detected mouse islet DNA spiked into mouse serum. This DMD assay was then applied to a mouse model of obesity and impaired glucose tolerance (IGT) followed longitudinally.

Figure 2E:
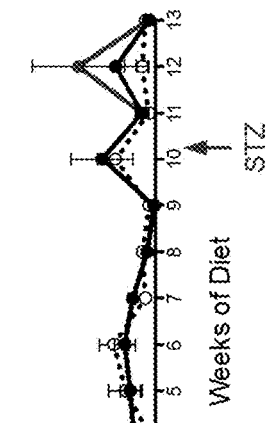
FIG. 2E depicts circulating unmethylated Ins2 DNA levels of C57BL/6J mice fed a low fat diet (LFD) or high fat diet (HFD) and treated with STZ to induce β cell death. N=6-12 mice total for each of 4 groups, done on two separate occasions. Data are presented as mean±SEM; *$P<0.05$ compared to LFD. #$P<0.05$ compared to no-STZ.
Figure 2F:
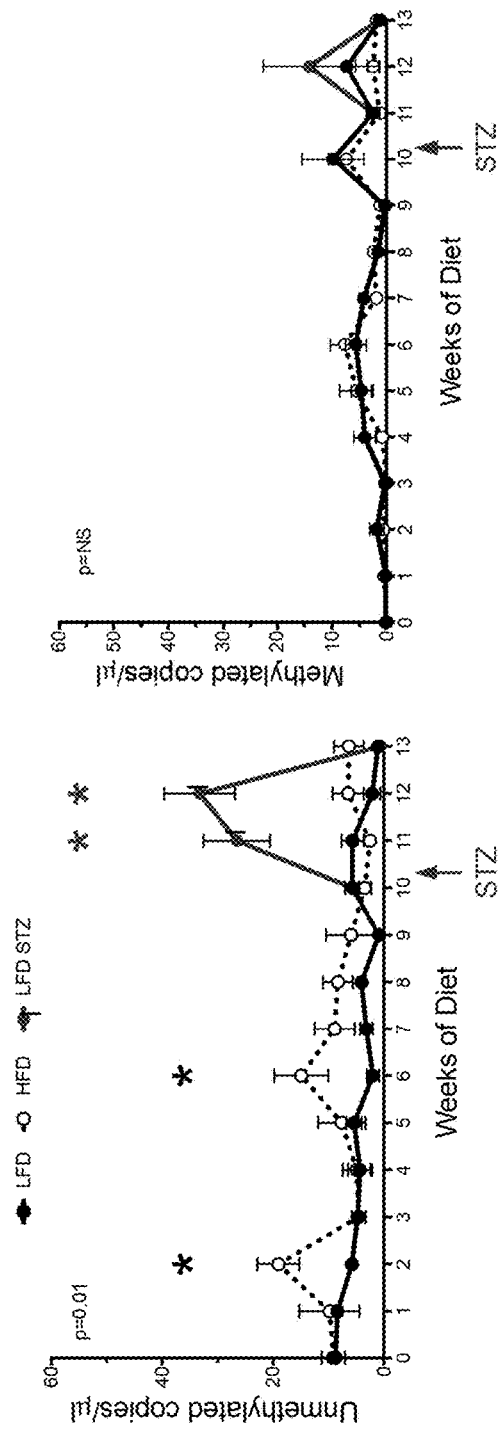
FIG. 2F depicts circulating methylated Ins2 DNA levels of C57BL/6J mice fed a low fat diet (LFD) or high fat diet (HFD) and treated with STZ to induce β cell death. N=6-12 mice total for each of 4 groups, done on two separate occasions. Data are presented as mean±SEM; *$P<0.05$ compared to LFD. #$P<0.05$ compared to no-STZ.

C57BL/6J mice were fed a high fat diet (HFD; 60% kcal from fat, 20% from protein, 20% from carbohydrate, Research Diets D12492) starting at 8 weeks of age and compared to control mice fed a low fat diet (LFD; 10% kcal from fat). HFD-fed mice exhibited statistically increased body weights and fasting blood glucose values compared to control LFD-fed animals beginning at 6 weeks after starting the diet (FIGS. 2A and 2B). Notably, HFD-fed mice showed IGT by glucose tolerance test (GTT) as early as 2 weeks after starting the diet (FIG. 2C). β cell mass quantified histologically increased significantly in HFD-fed animals compared to controls by 6 weeks post diet initiation (FIG. 2D). Compared to LFD-fed control animals, HFD-fed mice exhibited episodic increases in unmethylated Ins2 DNA levels at 2 and 6 weeks post diet initiation (FIG. 2E), coincident with the time points where glucose levels, fasting and by GTT were elevated (FIGS. 2B and 2C)). By contrast, methylated Ins2 DNA levels were not statistically different in HFD animals compared to controls across the feeding period. At 10 weeks after starting diet, mice were administered multiple low doses of STZ to induce overt 13 cell death. As shown in FIGS. 2E and 2F, both unmethylated and methylated Ins2 DNA levels increased significantly 1 week following STZ injections then declined to baseline levels.

Example 2

In this Example, the DMD assay was tested in a mouse model of spontaneous T2D.

Figure 3A:
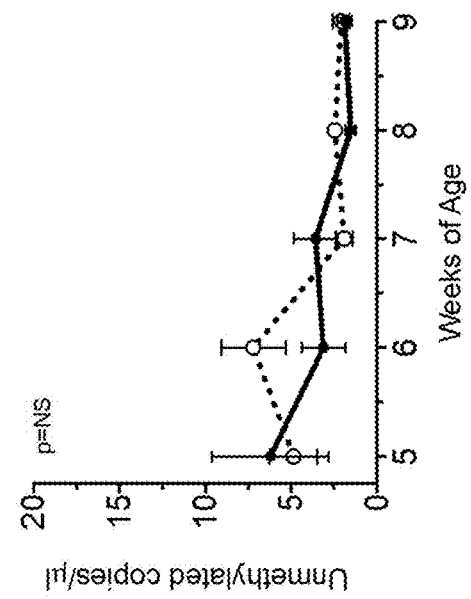
FIG. 3A depicts blood glucose levels of C57BLKS/J-db/db (db/db, N=16; open circles) and C57BLKS/J-db/+(db/+, N=16; closed circles) followed between 6-10 weeks of age.
Figure 3B:
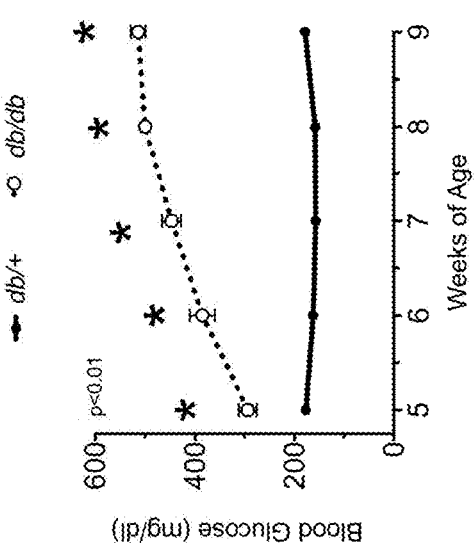
FIG. 3B depicts circulating unmethylated Ins2 DNA levels of C57BLKS/J-db/db (db/db, N=16; open circles) and C57BLKS/J-db/+(db/+, N=16; closed circles) followed between 6-10 weeks of age. Data are shown as mean±SEM, *P<0.05 compared to corresponding values in db/+animals.
Figure 3C:
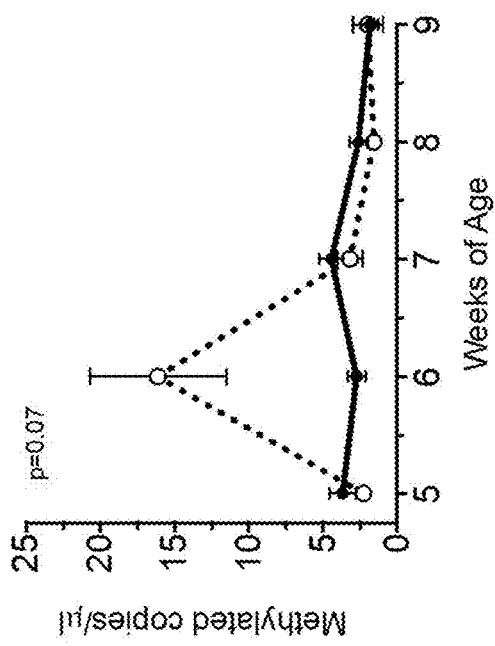
FIG. 3C depicts circulating methylated Ins2 DNA levels of C57BLKS/J-db/db (db/db, N=16; open circles) and C57BLKS/J-db/+(db/+, N=16; closed circles) followed between 6-10 weeks of age. Data are shown as mean±SEM, *P<0.05 compared to corresponding values in db/+animals.

The db/db mouse on the C57BLK/sJ background is an inbred strain that harbors a mutation in the leptin receptor gene and exhibits obesity, insulin resistance, β cell dysfunction, and diabetes as early as 6 weeks of age on a normal chow diet. Sera was serially collected from C57BLKS/J-db/db (henceforth referred to as "db/db") and control C57BLKS/J-db/+(henceforth referred to as "db/+") mice weekly from 6 to 10 weeks of age and subjected them to the DMD assay. As shown in FIG. 3A, db/db mice remained significantly hyperglycemic compared to db/+ controls throughout this timeframe. No statistically significant differences were seen in unmethylated Ins2 DNA (FIG. 3B). Methylated Ins2 DNA exhibited a significant increase in db/db compared to db/+ controls at 7 weeks of age, but returned to control levels thereafter (FIG. 3C). Collectively, these studies indicated that β cell death (as assessed by unmethylated Ins2 DNA levels) occurred episodically during the development of obesity and dysglycemia in mice and acutely upon β cell killing by STZ, but persistent β cell death was not detectable by the DMD assay in an animal model of established T2D (db/db).

Example 3

In this Example, the DMD assay was tested in samples from human cohorts.

Figure 4B:
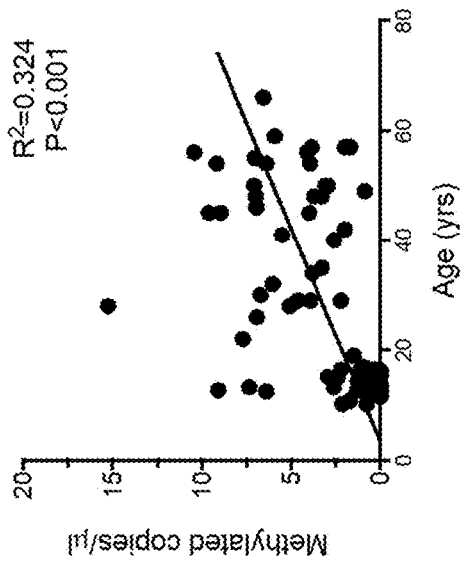
FIGS. 4A & 4B depicts regression analyses correlating clinical characteristics and circulating unmethylated (FIG. 4A) and methylated (FIG. 4B) INS DNA in human cohorts vs. age in healthy control individuals.
Figure 4A:
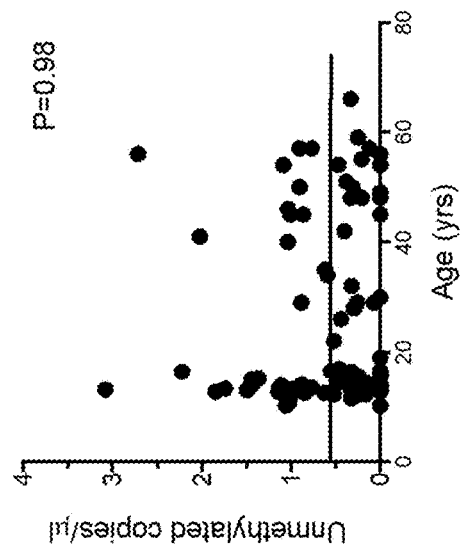
Figure 4C:
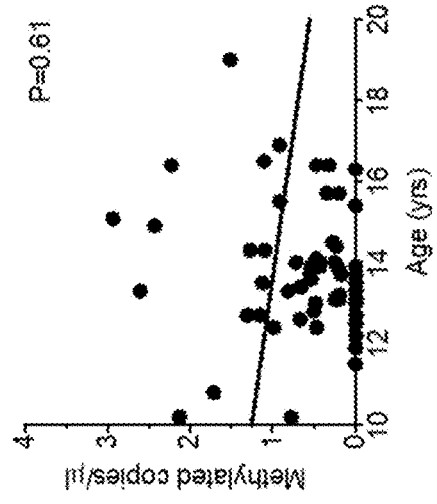
FIG. 4C-4F depicts regression analyses correlating clinical characteristics and circulating unmethylated (FIGS. 4C & 4E) and methylated (FIGS. 4D & 4F) INS DNA vs. age in youth (<21 years old) and adult (>21 years old) healthy control individuals.
Figure 4D:
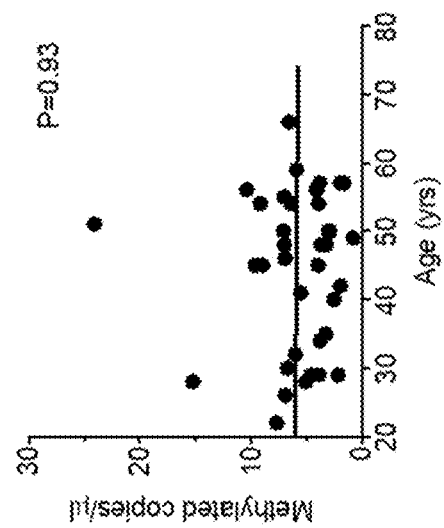
Figure 4E:
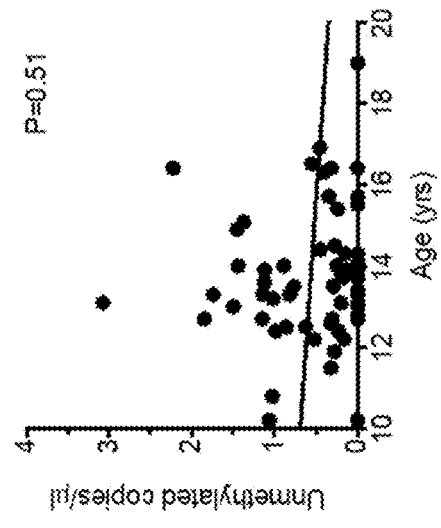
Figure 4F:
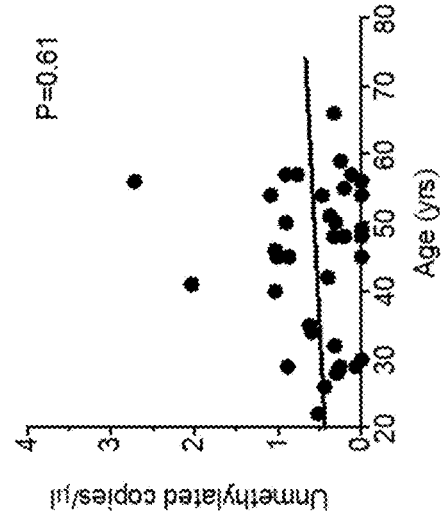
Figure 4G:
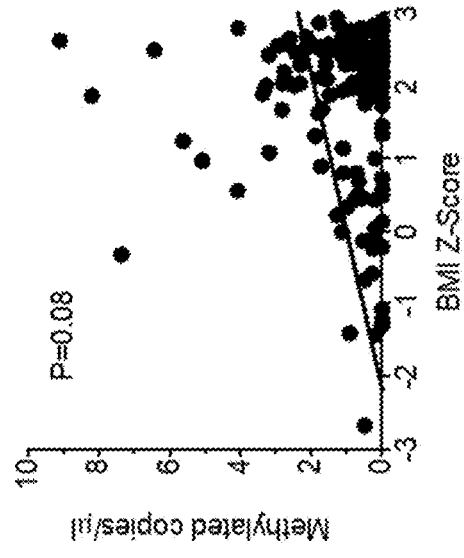
FIGS. 4G & 4J depicts regression analyses correlating clinical characteristics and circulating unmethylated (FIGS. 4G & 4I) and methylated (FIGS. 4H & 4J) INS DNA vs. BMI Z-Score or BMI in youths and adults.
Figure 4H:
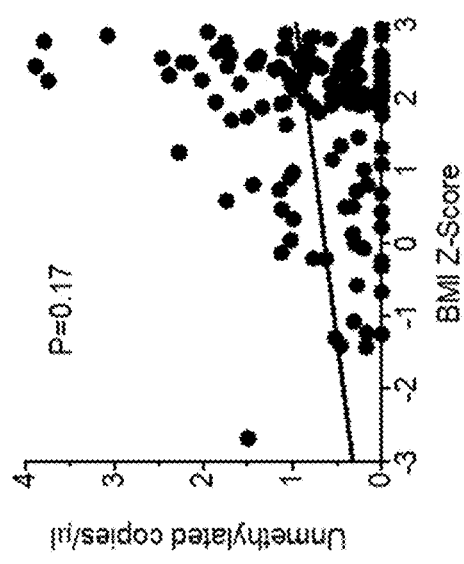
FIGS. 4K & 4N depicts regression analyses correlating clinical characteristics and circulating unmethylated (FIGS. 4K & 4M) and methylated (FIGS. 4L & 4N) INS DNA vs. HbA1C in youths and adults.
Figure 4I:
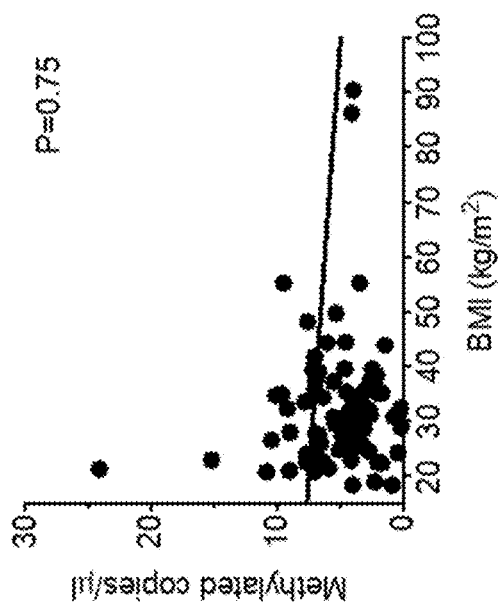
Figure 4J:
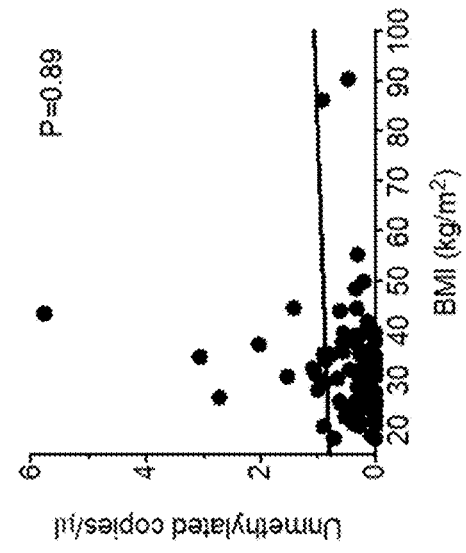
Figure 4K:
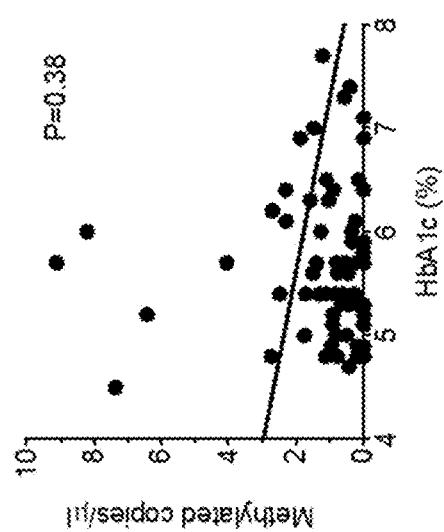
Figure 4L:
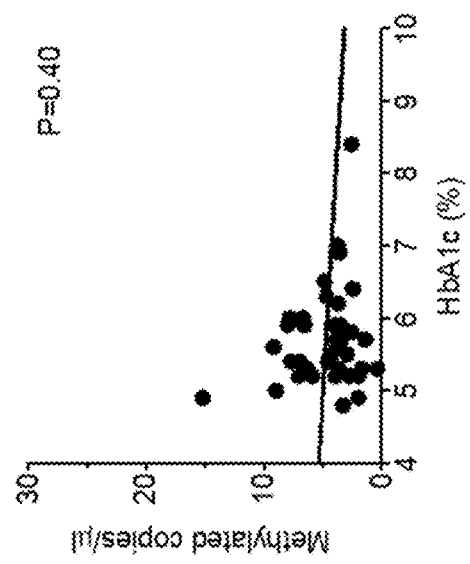
Figure 4M:
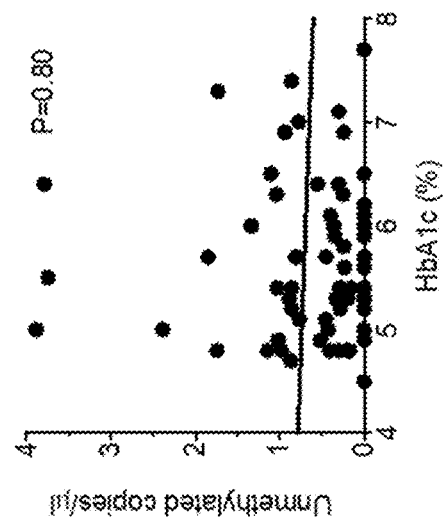
Figure 4N:
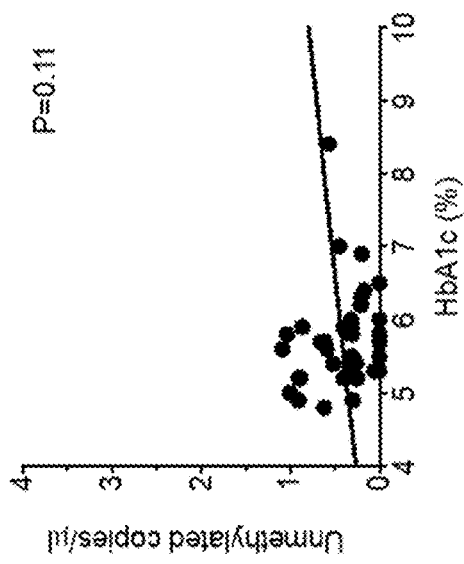

To apply the DMD assay to samples from human cohorts, the previously-validated DMD assay that interrogates differential methylation of cytosine at position −69 bp (relative to the transcriptional start site) in the human INS gene was used. Sera frozen at −80° C. from cross-sectional cohorts of healthy individuals and subjects with obesity, IGT and T2D, ages 10-66 years old were tested (see clinical characteristics of adults and youth in Tables 1 and 2, respectively). As shown in FIG. 4A, whereas unmethylated INS from healthy control subjects did not exhibit significant association with age, methylated INS exhibited a statistically significant increase with age (P<0.0001)(FIG. 4B). Consequently, youth (<21 years old) and adult (>21 years old) cohorts were separately analyzed. Within each cohort of healthy controls, there was no significant correlations of age with unmethylated or methylated INS (FIG. 4C). When considering each cohort including all participants without and with disease (healthy controls, obese, IGT, T2D), there were no significant correlations between unmethylated or methylated INS and BMI/BMI Z-score (FIG. 4D) or HbA1c % (FIG. 4E).

Example 4

In this Example, unmethylated and methylated INS DNA in adults and youths with obesity, IGT, and T2D was determined.

The adult cohorts were stratified into 4 groups: lean controls with normal glucose tolerance (NGT); overweight/obese with normal glucose tolerance (OB-NGT); impaired glucose tolerance (IGT); and type 2 diabetes mellitus (T2D). The clinical characteristics of these groups are shown in Table 1.

TABLE 1

Demographic and Laboratory Evaluation of Adult Cohorts.

|  | NGT | OB-NGT | IGT | T2D | P value |
| --- | --- | --- | --- | --- | --- |
| Total (% male) | 24 (54) | 39 (62) | 38 (58) | 16 (68) |  |
| Age, years | 40 ± 4.1 | 46 ± 1.9 | 46 ± 1.8 | 49 ± 2.8 | 0.30 |
| BMI, kg/m$^2$ | 21.7 ± 0.57 | 33.8 ± 2.54 | 31.5 ± 1.32 | 38.7 ± 3.73 | <0.001 |
| Fasting glucose, mg/dL | 84.2 ± 1.30 | 90 ± 6 | 104 ± 10.5 | 136 ± 16 | <0.001 |
| 2 hr OGTT glucose, mg/dL | 94.9 ± 8.04 | 104 ± 19 | 140 ± 24.5 | 262 ± 33 | <0.001 |

Figure 5A:
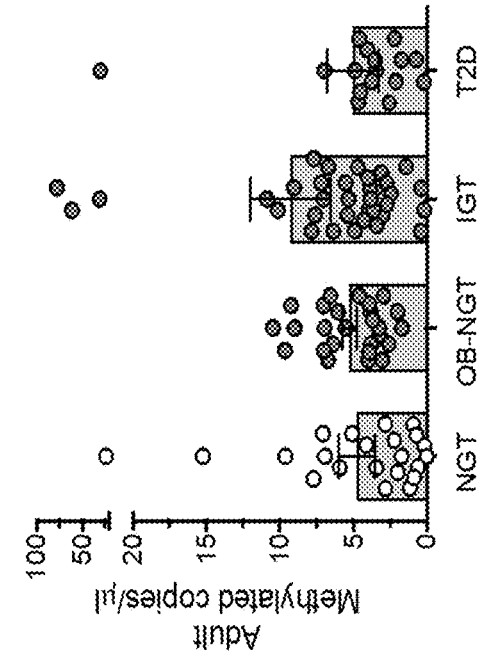
FIG. 5A depicts circulating unmethylated INS DNA in adult lean controls with normal glucose tolerance (NGT) and cohorts with obesity and normal glucose tolerance (OB-NGT), impaired glucose tolerance (IGT) and type 2 diabetes (T2D). Data are presented as mean±SEM. *P<0.05 for the comparisons indicated.
Figure 5B:
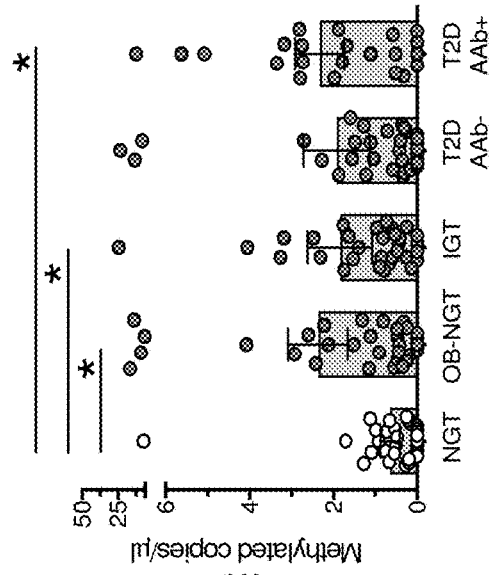
FIG. 5B depicts circulating methylated INS DNA in adults with NGT, OB-NGT, IGT, and T2D. Data are presented as mean±SEM. *P<0.05 for the comparisons indicated.

As shown in FIGS. 5A and 5B, in this cross-sectional comparison none of the adult groups showed statistically significant differences in unmethylated (FIG. 5A) or methylated (FIG. 5B) INS DNA compared to healthy controls. The youth cohorts were stratified into the same groups as the adults, but the T2D group was separated into autoantibody-negative (AAb−) and autoantibody-positive (AAb+) phenotypic T2D groups, given the high prevalence of T1D in this age population. The clinical characteristics of these groups are shown in Table 2.

TABLE 2

Demographic and Laboratory Data of Youth Cohorts

|  | NGT | OB-NGT | IGT | AAb− T2D | AAb+ T2D | P value |
|---|---|---|---|---|---|---|
| Total (% male) | 32 (56) | 31 (35) | 31 (35) | 34 (47) | 22 (45) |  |
| Age, years | 13 ± 0.2 | 14 ± 0.3 | 15 ± 0.4 | 15 ± 0.3 | 14 ± 0.5 | <0.001 |
| BMI, Z-Score (ZS) | −0.14 ± 0.15 | 2.21 ± 0.10 | 2.33 ± 0.06 | 2.39 ± 0.05 | 1.90 ± 0.12 | <0.001 |
| HbA1c (%) | 5.3 ± 0.1 | 5.4 ± 0.1 | 5.4 ± 0.1 | 6.6 ± 0.1 | 6.3 ± 0.2 | <0.001 |
| Fasting glucose, mg/dL | 95.3 ± 3.5 | 90.8 ± 3.5 | 92.5 ± 3.5 | 115.1 ± 3.4 | 129.1 ± 5.0 | <0.001 |
| 2 hr OGTT glucose, mg/dL | N/A | 111.4 ± 10.5 | 158.8 ± 8.4 | 197.5 ± 8.1 | 299.1 ± 12.1 | <0.001 |
| Treatment modality n (%) |  |  |  |  |  |  |
| Lifestyle |  |  |  | 7 (21) | 2 (13) |  |
| Insulin |  |  |  | 4 (12) | 3 (19) |  |
| Metformin |  |  |  | 16 (47) | 2 (13) |  |
| Insulin & Metformin |  |  |  | 7 (21) | 9 (56) |  |

Figure 5C:
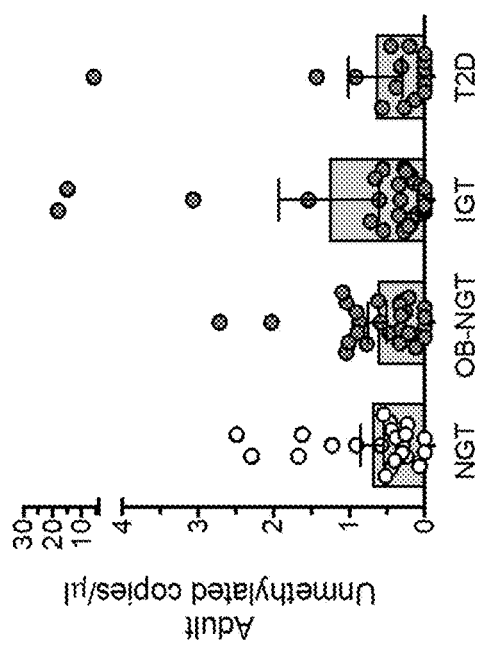
FIG. 5C depicts circulating unmethylated INS DNA in youth lean controls (NGT) and obese youth with normal glucose tolerance (OB-NGT), IGT and clinician diagnosed T2D without autoantibodies (T2D-AAb−) and T2D with autoantibodies (T2D-AAb+). Data are presented as mean±SEM. *P<0.05 for the comparisons indicated.
Figure 5D:
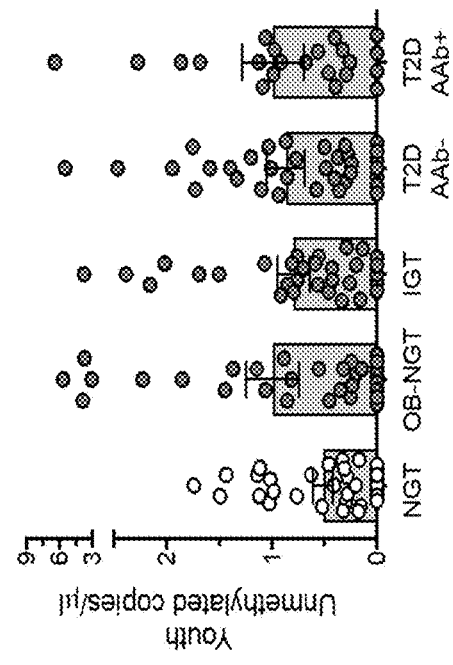
FIG. 5D depicts circulating methylated INS DNA in youth with NGT, OB-NGT, IGT, T2D-AAb−, T2D-AAb+. Data are presented as mean±SEM. *P<0.05 for the comparisons indicated.

As shown in FIG. 5C, there were no statistical differences in unmethylated INS DNA among these cross-sectional cohorts of youths. By contrast, however, FIG. 5D shows that methylated INS DNA was significantly elevated in obese youth with NGT (P=0.03), IGT (P=0.04), and T2D-AAb+ (P=0.002) compared to healthy non-obese controls.

Example 5

In this Example, differentially methylated INS DNA was determined in inflammation and autoimmunity.

Figure 6A:
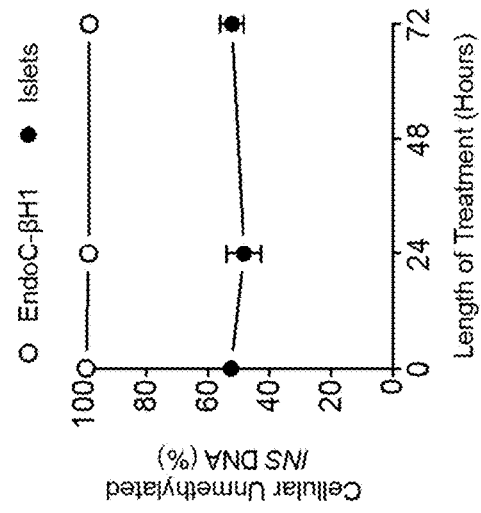
FIG. 6A depicts the determination of unmethylated INS DNA as a percentage of total INS DNA released into the medium from EndoC-βH1 and human islets treated with cytokine mix (IL-1β and IFN-γ) for the indicated times. Data are presented as mean±SEM. *P<0.05 compared to Control.
Figure 6B:
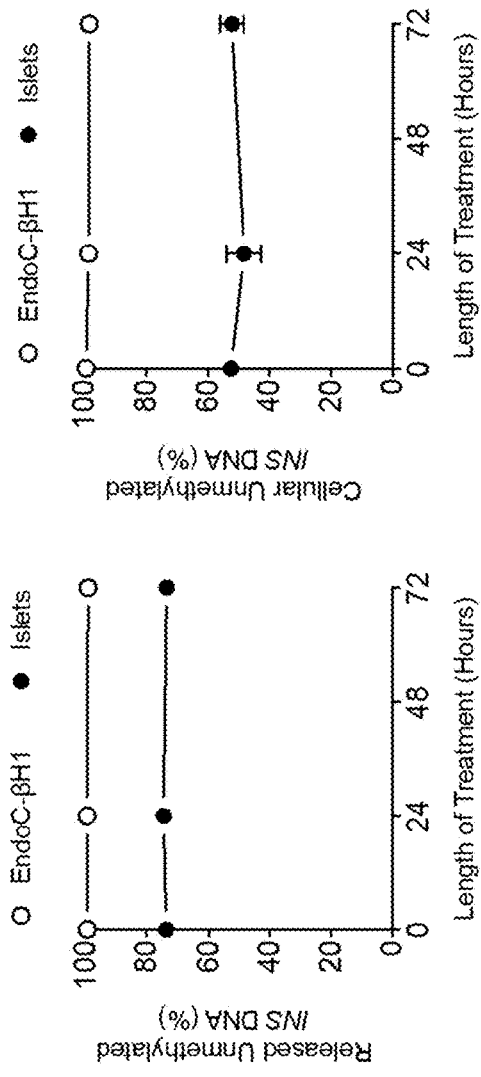
FIG. 6B depicts unmethylated INS DNA as a percent of total INS DNA in the cellular fraction of EndoC-βH1 cells and human islets following treatment with cytokine mix (IL-1β and IFN-γ). Data are presented as mean±SEM. *P<0.05 compared to Control.

The elevation in cell-free methylated INS in T2D-AAb+ individuals is reminiscent of the elevations reported in youth with new-onset T1D (Fisher et al. Diabetes. 2015 November; 64(11):3867-72). To determine if inflammation increased the frequency of methylation at INS position −69 bp, time course incubations of the human β cell line EndoC-βH1 and primary human islets was performed with proinflammatory cytokines IL-1β and IFN-γ, differential methylation was then interrogated by the DMD assay in the cell-free supernatant (released DNA from dying cells) and in cells directly. As shown in FIG. 6A, unmethylated INS (as a percentage relative to total INS) released into the medium was unchanged during the incubation time course. In agreement with this finding, the percentage of unmethylated INS was also unchanged in cells themselves (FIG. 6B), indicating that methylation frequency at position −69 bp at the INS gene was not impacted by inflammation in β cells.

To further determine the relationship between inflammation and methylated INS DNA levels, the DMD assay was applied to serum from youth with an active organ-specific inflammatory disorder (inflammatory bowel disease, IBD) and with generalized inflammation (sepsis requiring intensive care unit-level care and with some requiring insulin therapy) (see Table 3).

TABLE 3

Demographic and Laboratory Evaluation of IBD and Sepsis cohorts.

|  | Control | IBD | Sepsis | P value |
|---|---|---|---|---|
| Total (% male) | 10 (60) | 11 (45) | 10 (60) |  |
| Age, years | 14 ± 0.6 | 14 ± 0.9 | 11 ± 1.4 | 0.98 |

Figure 6C:
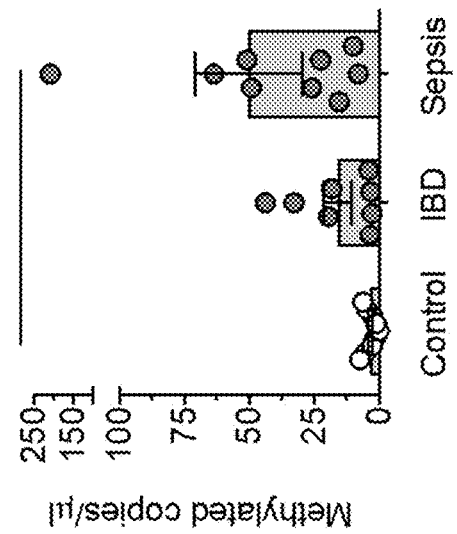
FIG. 6C depicts circulating unmethylated INS DNA in healthy youth (Control) and youth with inflammatory bowel disease (IBD) and Sepsis. Data are presented as mean±SEM. *P<0.05 compared to Control.
Figure 6D:
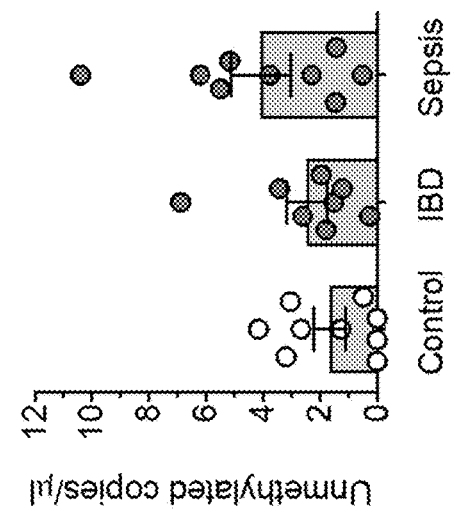
FIG. 6D depicts circulating methylated INS DNA in Control youth and youth with IBD and Sepsis. Data are presented as mean±SEM. *P<0.05 compared to Control.
Figure 7A:
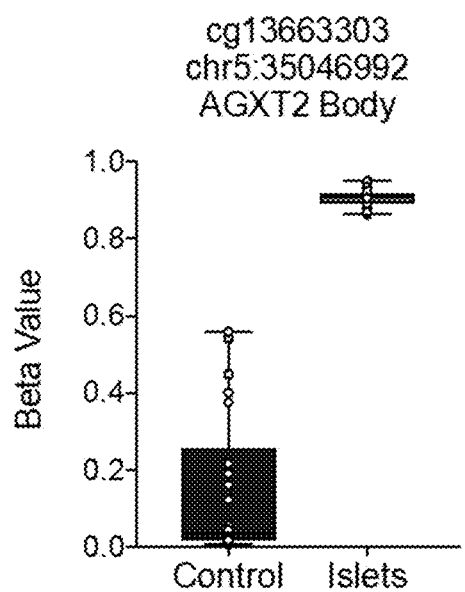
FIGS. 7A-7J: Methylation status of differentially methylated genes. Infinium HumanMethylation 450 array was performed on bisulfite-treated DNA from 64 human islet samples and compared to data from 27 human non-islet tissues obtained from online datasets. Informatics analysis of these datasets identified 2534 hypomethylated CpG sites and 3667 hypermethylated CpG sites in human islets vs. non-islet tissues. Graphs providing the data for the top 10 differentially methylated CpG sites are provided in FIGS. 7A-7J.
Figure 7B:
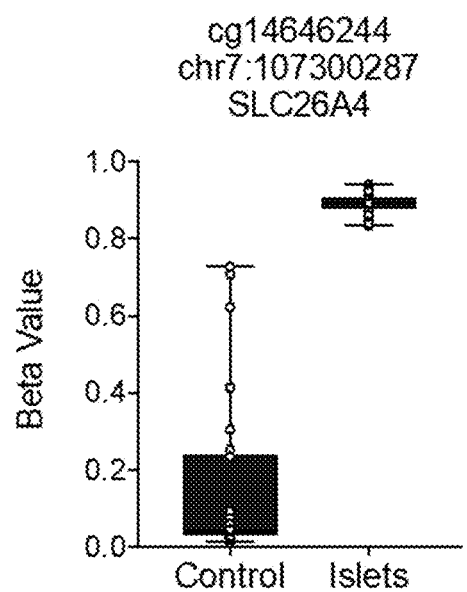
Figure 7C:
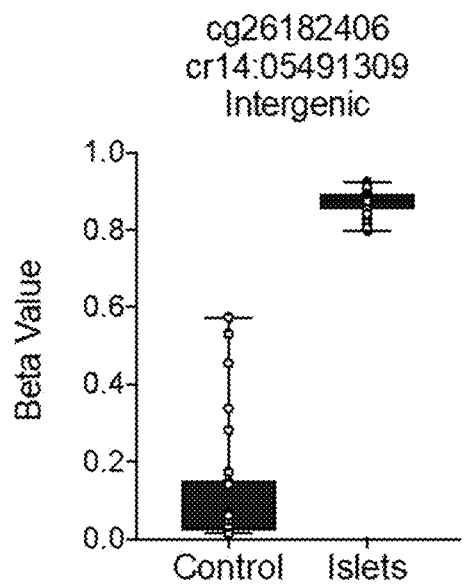
Figure 7D:
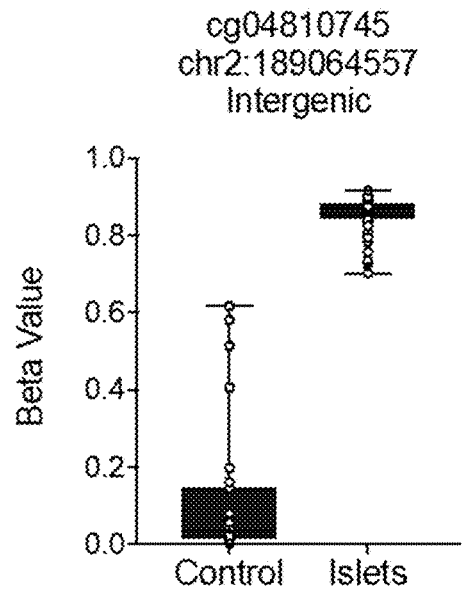
Figure 7E:
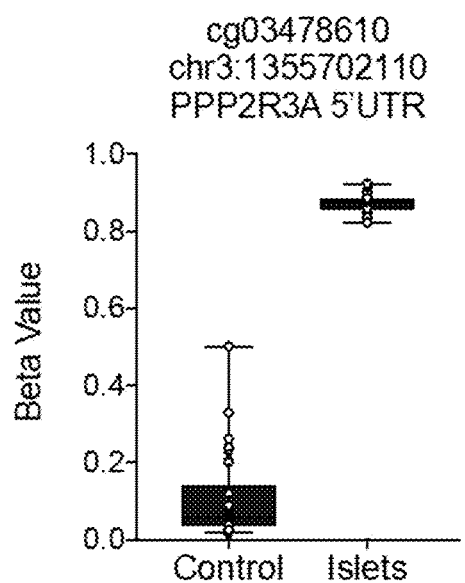
Figure 7F:
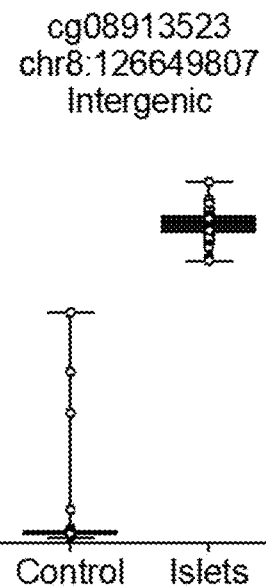
Figure 7G:
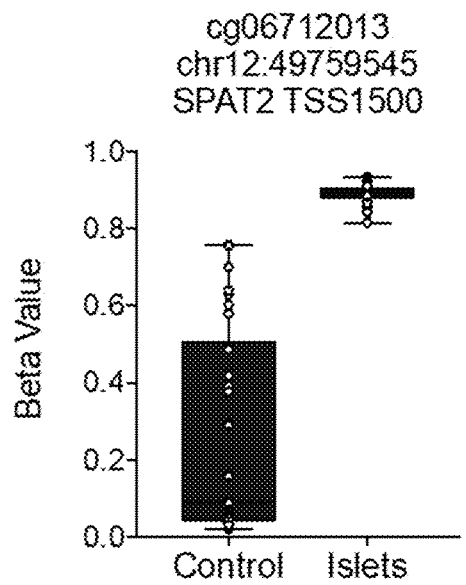
Figure 7H:
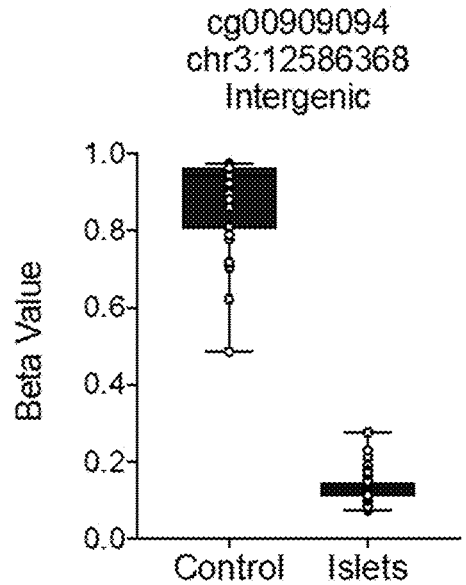
Figure 7I:
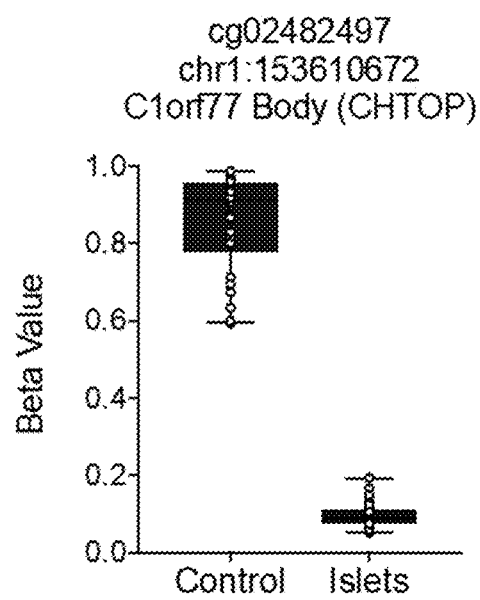
Figure 7J:
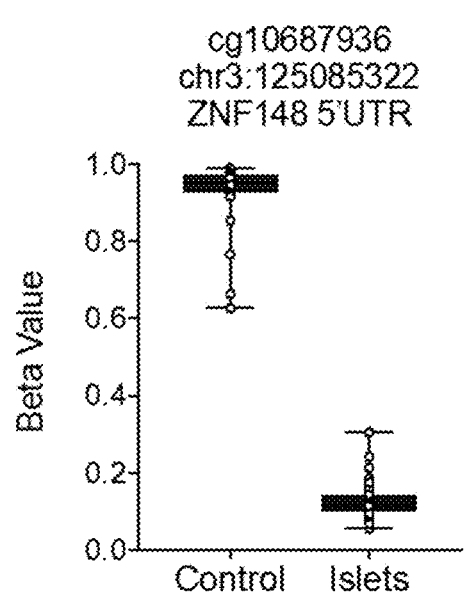

As shown in FIGS. 6D and 6E, compared to controls, subjects with sepsis exhibited elevations in methylated (P<0.001) INS DNA levels but not unmethylated INS DNA, whereas subjects with IBD exhibited no statistically significant elevations in either DNA species.

These Examples applied the DMD assay to quantify circulating levels of unmethylated and methylated INS across a spectrum of states from obesity to T2D in mouse models and in cross-sectional cohorts of youth and adults. These Examples provide several new findings, notably (a) circulating unmethylated INS, a biomarker of β cell death, increased episodically and transiently during the development of obesity and glucose intolerance in mice, but was not persistently elevated in established T2D, (b) in cross-sectional cohorts of adults and youth with obesity and T2D, sustained β cell death was not evident, and (c) in youth, elevations in circulating methylated INS was a biomarker of aggressive inflammatory states.

Example 6

In this Example, differentially methylated CHTOP DNA was determined to be a biomarker for detecting β-cell DNA.

Circulating cell-free unmethylated DNA fragments arising from the human INS gene have been proposed as biomarkers of β-cell death for the presymptomatic detection of diabetes. However, given the variability of CpG methylation in the INS gene in different cell types, this gene alone may not yield sufficiently specific information to unambiguously report β-cell damage. As disclosed herein an unbiased approach was employed, using data from a human DNA methylation gene array, resulting in the identification of the CHTOP gene as a biomarker whose CpGs show a greater frequency of unmethylation in human islets. When tested across an array of non-islet human tissues by digital PCR, both INS and CHTOP contain unmethylated CpG sites in several of these tissues, but in a non-overlapping pattern: INS showed a slightly higher frequency of unmethylation in adipose tissue, whereas CHTOP appeared to be unmethylated in pancreas, brain, and skeletal muscle. Notably, INS and CHTOP genes are both unmethylated in human β cells and α cells, indicating that each species represent markers of islet cell death in general, and together can be used to distinguish death arising from islets vs. other tissues. To validate unmethylated CHTOP as a biomarker for islet cell damage, we used digital PCR to measure cell-free circulating DNA in human populations. Compared to healthy controls, we observed that levels of differentially methylated CHTOP and INS were higher in youth with new onset type 1 diabetes and in healthy youth who have first-degree relatives with type 1 diabetes. When tested in youth across a spectrum of metabolic dysfunction, increased levels of unmethylated INS and CHTOP were observed in obese individuals compared to lean controls. Together, these data suggest that simultaneous measurement of both INS and CHTOP is likely to detect β-cell death in T1D and raise new questions about beta cell health in populations at risk for both T1D and T2D development.

In an ongoing effort to address the current limitations of differentially methylated INS as a biomarker for islet cell damage, this present study utilizes a comprehensive high throughput screening approach to identify new differentially methylated DNA targets in human islets. Using DNA deep sequencing, we revealed that chromatin target of PRMT1 (CHTOP; SEQ ID NO: 14) exhibits a high degree of unmethylation in primary human islets, but not in non-islet tissues. Next, we validated our existing INS DMD assay and our newly developed CHTOP DMD assay in healthy controls and pediatric patients with new onset T1D with known islet cell damage. We further tested both assays in cohorts of pediatric patients with and at risk for T1D and T2D to assess the use of multiple DNA species as biomarkers for future clinical disease development.

Cell Purification

Dissociation of human islets was achieved by incubation with accutase (Millipore) supplemented with 5 U/ml of DNAse 1 at 37° C. for 10-15 min. The dissociated cells were washed with 1% BSA in PBS and cultured in islet standard medium (Prodo labs) and followed by Newport Green labeling (Lukowiak, et al. J Histochem Cytochem 2001; 49:519-27). β cells and non β cells were sorted by positive or negative Newport Green staining (respectively) using a BD FACSAria cell-sorter (BD Biosciences). The quality of the sorted cells was further confirmed by immune fluorescence staining of insulin and glucagon.

Methylation-Specific DNA Sequencing

DNA was analyzed using a methylation specific Infinium HumanMethylation450 array (Illumina) of 64 human islet preparations and compared with 27 human tissues/cell lines that were analyzed using publicly available datasets.

DNA was isolated from FACS sorted human β cells, endoC βH1 cells, and tissues (brain, heart, lung, thyroid, spleen, intestine, skin, skeletal muscle, adipose, pituitary, pancreas and liver) following manufacture's protocol (Gen-Elute, Mammalian Genomic DNA Miniprep Kits, Sigma-Aldrich, USA). Following isolation, DNA was bisulfite treated (EZ DNA Methylation-Lightning Kit, Zymo Research, USA1). Details regarding selected differentially methylated CpGs are provided in Table 4.

TABLE 4

Selected differentially methylated CpG; position are in hg19/GRCh37 genome assembly

| IlmnID | deltaBeta | adj.pval | CHR | MAPINFO | Strand | UCSC RefGene_Name | UCSC RefGene Accession | UCSC RefGeneGroup |
|---|---|---|---|---|---|---|---|---|
| cg04810745 | 0.831644533 | 1.93E−12 | 2 | 189064557 | R | NA | NA | NA |
| cg03478610 | 0.818905576 | 1.67E−15 | 3 | 135702110 | R | PPP2R3A | NM_002718 | 5'UTR |
| cg08913523 | 0.808456353 | 1.39E−14 | 8 | 126649807 | F | NA | NA | NA |
| cg06712013 | 0.804127303 | 1.14E−10 | 12 | 49759545 | R | SPATS2 | NM_023071 | TSS1500 |
| cg02482497 | −0.818994841 | 3.22E−16 | 1 | 153610672 | R | C1orf77 | NM_015607 | Body |

Materials and Methods

Human Tissues, Human Islets, and Cell Lines

Human non-pancreatic tissue samples were obtained from National Disease Research Interchange (NDRI). Pancreatic tissue samples were obtained from cadaveric donors who were not suitable for transplantation (University of Pisa). Human islets were obtained from the Integrated Islet Distribution Program (IIDP). Human islets and endoC βH1 cells and were cultured with or without cytokines (50 U/ml IL-1β and 1000 U/ml IFN-γ) for 24 hours and used for downstream applications.

PCR was performed using primers specifically designed to amplify bisulfite converted DNA (See Table 5). PCR products were purified using a QIAquick PCR purification kit (Qiagen) and DNA was quantified using a Qubit dsDNA assay kit (Invitrogen). Equal amounts of DNA were used for library preparation. Fully methylated or unmethylated synthetic DNA were used as a positive control to calculate the degree of methylation. Methylation specific DNA sequencing was performed using an Ion Proton System (LifeTechnologies).

TABLE 5

| Illumina ID | UCSC_RefGene Name | Forward Primer | Reverse Primer |
|---|---|---|---|
| cg04810745 | NA | TGTTGAGTTTAGAAGTTAAGTTGGA SEQ ID NO: 15 | ACAATACCCCTAAAATACAAAA SEQ ID NO: 16 |
| cg03478610 | PPP2R3A | AGAGGTGGTAATTTAGGTTTGTGT SEQ ID NO: 17 | ACCATCACAATTTACTCATCCTCA SEQ ID NO: 18 |
| cg08913523 | NA | GGTTTTGTGGGTTGGAAGTTAG SEQ ID NO: 19 | ACCACCCCCTCCTTCAACTA SEQ ID NO: 20 |

TABLE 5-continued

| Illumina ID | UCSC_RefGene Name | Forward Primer | Reverse Primer |
|---|---|---|---|
| cg06712013 | SPATS2 | ATGGTTGGAGTAGATGAGAT SEQ ID NO: 21 | ACACCACTACACTCCACCCT SEQ ID NO: 22 |
| cg02482497 | C1orf77 | TGTTGTGAGTTTTGAAGGTGTT SEQ ID NO: 23 | ACCCATTCTCTCACCTACTT SEQ ID NO: 24 |

Plasmid Synthesis

Unmethylated and methylated plasmids were synthesized using a TOPO™ TA Cloning kit (Thermo Fisher) from DNA from β cells and non-β cells. DNA from bacteria was isolated using an QIAprep Spin Miniprep kit (Qiagen). The plasmid sequence was confirmed by DNA sequencing using M13R primers.

Methylation Specific Multiplex ddPCR Assay

TaqMan® based dual-fluorescent probes were designed for the interrogation of differential methylation pattern at CpG site Chr1:153610817 of the CHTOP gene (forward: 5'-TTTGGAGTTTTTGGTTTAGTAAGTTAT-GAAAATGTT (SEQ ID NO: 10); reverse: 5'-CATC-TACTAAACCAATCTTCTATTTCTAACACTAACTAA (SEQ ID NO: 11); VIC probe: 5'-AAACCCGAATATTCAC (SEQ ID NO: 12); FAM probe: 5'-AAACCCAAATATT-CAC (SEQ ID NO: 13)). Assay linearity was determined by serial dilution of unmethylated and methylated plasmids.

Human Subjects.

Frozen serum samples from 150 youth ages 10 to <20 years old who participated in NIH-funded K24 grant of "Childhood Insulin Resistance" were used in the present analysis. A 2-hr OGTT was performed in obese participants as described before (Burns et al Diabetes Care 2011; 34:2033-40). GAD 65 kDa autoantibody and insulinoma-associated protein 2 autoantibody (IA2) were measured using the NIDDK standardized assay protocol as described before (Tfayli et al, Diabetes Care 2010; 33:632-8). Participants with diabetes were on either lifestyle only, or metformin or metformin plus insulin.

DNA Isolation and Bisulfite Conversion.

DNA from tissue and cell samples was isolated using GenElute Mammalian Genomic DNA Miniprep Kit (Sigma-Aldrich). DNA from serum was isolated from 50 µl of serum samples spiked in with 5 µg carrier DNA (poly-A) using QIAamp DNA Blood Mini Kit (Qiagen). DNA recovery from serum samples (of the poly-A carrier) was quantified using a nano photometer (Implen). All samples showed ≥85% recovery of DNA following isolation. DNA bisulfite conversion was carried out using EZ DNA Methylation-Lightning kit (Zymo Research), and conversion was verified using a pre- and post-conversion sample in the ddPCR.

Statistical Analysis.

All data are presented as mean±SEM. For analysis of methylated and unmethylated INS DNA levels, a Kruskal-Wallis (non-parametric) test was employed followed by a Dunnett's post-test (to compare values to healthy controls). Associations were measured by linear regression modeling. GraphPad Prism Version 7.0c (GraphPad Software) was used for statistical analyses of sample data. Statistical significance was assumed at P<0.05.

Results

Identification of Differentially Methylated Genes from Isolated Human Islet DNA

To identify additional genes that are differentially methylated in primary human β-cells, we employed a comprehensive unbiased approach. DNA was isolated from 64 different human preparations, bisulfite treated to convert unmethylated cytosols to uracils, and methylation status was determined using an Infinium HumanMethylation450 array. The data was then compared to publicly available datasets from 27 non-islet human tissues. Informatics analysis of these datasets identified 2534 hypomethylated CpG sites and 3667 hypermethylated CpG sites in human islets vs. non-islet tissues. The 10 most highly differentially methylated genes are shown in FIGS. 7A-7J. To verify the methylation status of the identified genes, we performed PCR amplification of a 0.5 kb segment surrounding 5 of the differentially-methylated CpG sites using bisulfite-treated DNA from FACS-purified primary human β cells (using Newport Green selection) from 3 different islet preparations, the EndoC-βH1 human fetal β-cell-derived line, and 11 non-islet tissues. Products were pooled and deep-sequenced using an Ion Proton System and methylation status was determined. Interestingly, analysis revealed that only one gene, CHTOP (C1orf77), which encodes chromatin target of PRMT1, was found to be differentially methylated in primary human β cells alone (48-99% hypomethylated), compared to non-islet tissues samples and the human β-cell line. To determine stability of the CpG site, β cells were treated with cytokines (IFN-γ and IL-1β) to mimic diabetes stress conditions. The CpG sites within the CHTOP gene did not differ with cytokine treatment, suggesting that CHTOP is an ideal candidate to develop a DMD assay to measure islet cell damage.

Next, we developed PCR TaqMan probe-based DMD assays to quantitatively measure differential methylation CHTOP gene at Chr1:153610817 using the sensitive reproducible droplet digital PCR (ddPCR) technique that allows for absolute quantitation of DNA copy numbers (Hindson et al, Nat Methods 2013; 10:1003-5). Comparison of the CHTOP site with our previously validated INS assay, showed both CHTOP and INS are hypermethylated in non-islet tissues, and hypomethylated in islet cells. Both CHTOP and INS are hypomethylated in islets, whereas CHTOP is hypomethylated in the pancreas and INS is hypermethylated. Additionally, there is little change to percent methylation of islets treated with cytokines or harvested from individuals with diabetes.

Figure 8A:
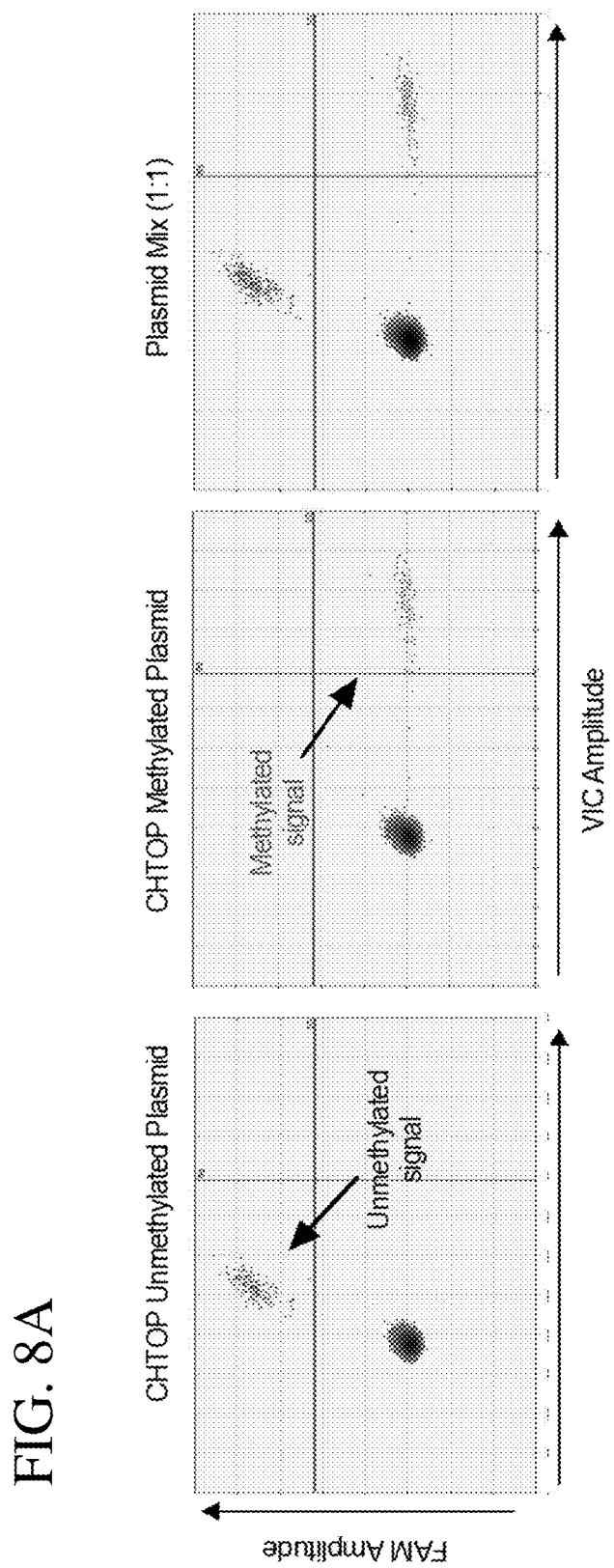
FIGS. 8A-8F: Differentially-methylated DNA PCR assay validation. Dilutions of plasmids containing cloned, bisulfite-converted unmethylated and methylated CHTOP DNA were subjected to ddPCR, and 2-D plots from ddPCR are present in FIG. 8A, and quantitation of plasmid dilution curves, presented as copies/µl are provided in FIG. 8B. Islet DNA was added to serum and dilution curves were generated for unmethylated CHTOP and INS DNA (FIGS. 8C & 8D) and for methylated CHTOP and INS DNA (FIGS. 8E & 8F).
Figure 8B:
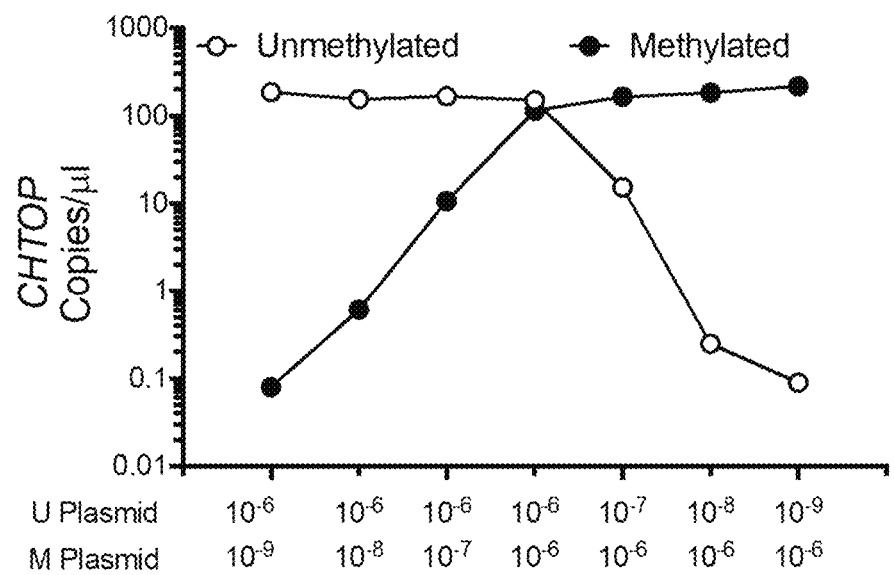
Figure 8C:
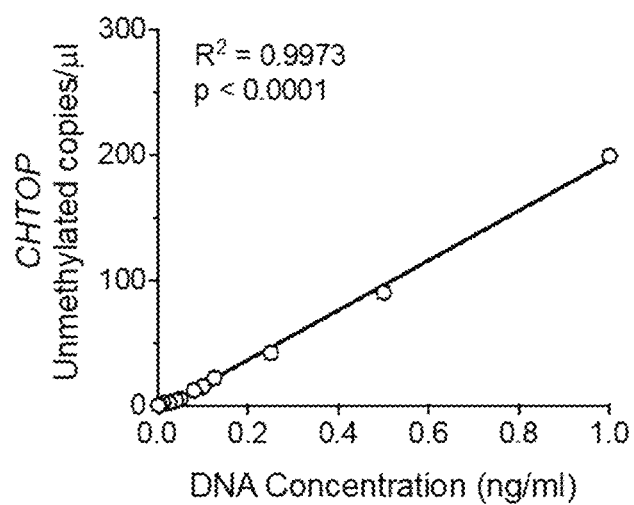
Figure 8D:
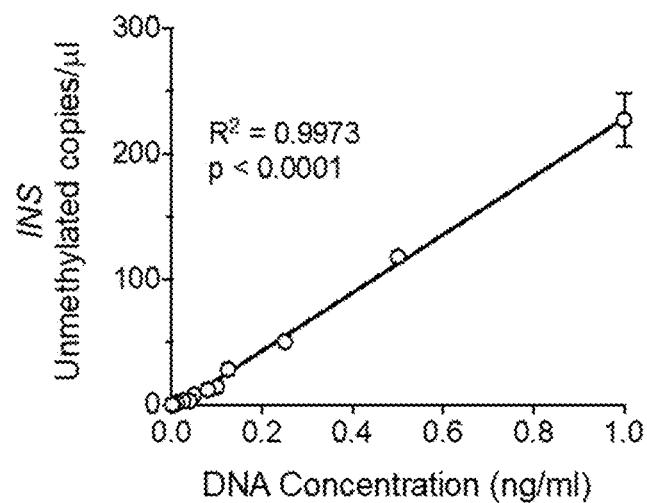
Figure 8E:
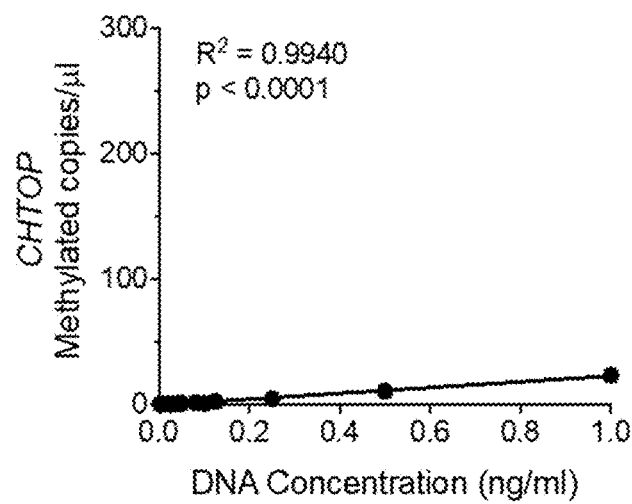
Figure 8F:
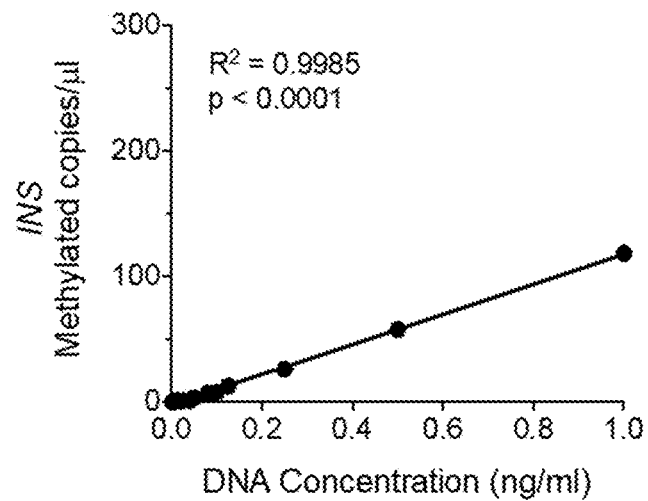
Figure 9A:
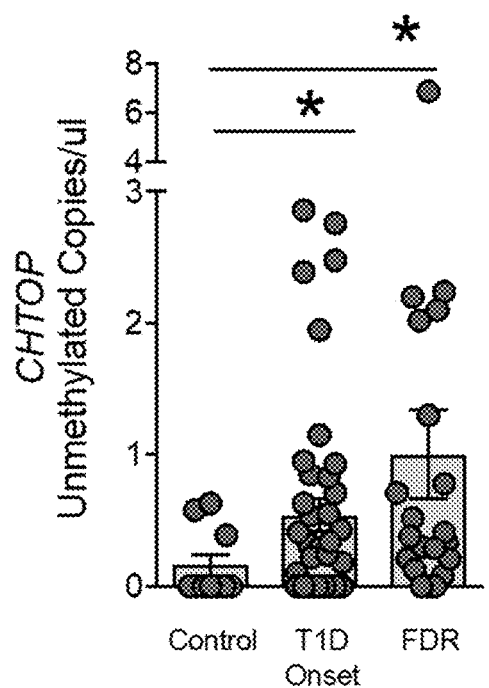
FIGS. 9A-9D: Circulating CHTOP and INS DNA levels in control, new onset T1D, and first degree relatives (FDR) of individuals with T1D.
Figure 9B:
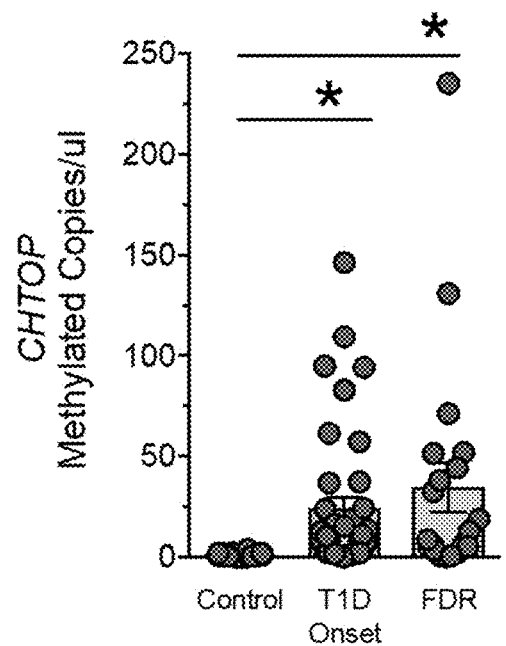
Figure 9C:
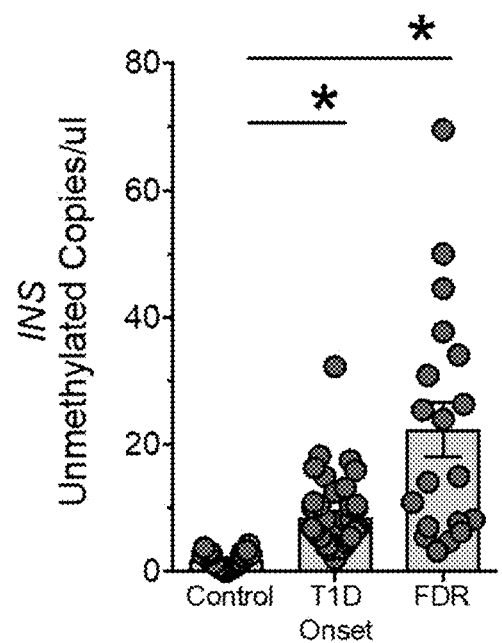
Figure 9D:
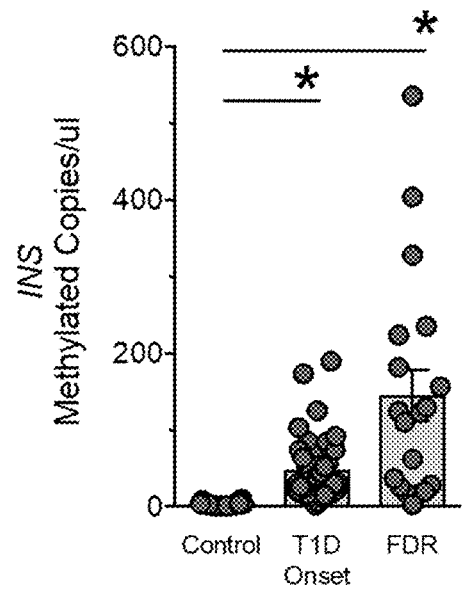

To determine the sensitivity and linearity of our CHTOP DMD assay, we first mixed varying proportions of the cloned unmethylated and methylated plasmids of the CHTOP gene. As shown in FIGS. 8A and 8B, we were able to detect both unmethylated and methylated CHTOP DNA. To assess linearity of our assays, DNA from the human β-cell-derived line EndoC-βH1 (predominately unmethylated INS DNA) or the human kidney-derived cell line 293T (predominately methylated INS DNA) was spiked into serum from a healthy human subject. The serum was then serially diluted (into healthy unspiked human serum) and INS and CHTOP DMD were measured. Linearity was established for both methylated and unmethylated INS and CHOP DMD; however, the sensitivity of the methylated CHTOP assay displayed reduced sensitivity compared to those of unmethylated CHTOP and methylated and unmethylated INS.

Assessment of Unmethylated and Methylated CHTOP and INS DNA in Youth with T1D

Next, to validate our assay in subjects with known islet cell damage, we applied both the CHTOP and INS DMD assays to a cohort of subjects with new-onset T1D and compared them to healthy control subjects. Relevant demographic and laboratory information are presented in Table 6.

TABLE 6

Demographic Data of Youth T1D and FDR Cohort

|  | Control | FDR | New Onset T1D |
|---|---|---|---|
| Total (% male) | 10 (50) | 23 (57) | 43 (59) |
| Age, years | 11 ± 1.1 | 10 ± 0.4 | 7.4 ± 0.6 |

As shown in FIGS. 9A-9D, both unmethylated and methylated CHTOP and INS DNA were significantly higher in subjects with new onset T1D compared to healthy controls. Surprisingly, when tested in first degree relatives (FDR) of patients with T1D who did not have diabetes or evidence of islet autoimmunity (antibody negative), both unmethylated and methylated CHTOP and INS were also significantly increased compared to unrelated healthy control subjects (FIGS. 9A-9D).

Assessment of Unmethylated and Methylated CHTOP and INS DNA in Obese Youth

Figure 10A:
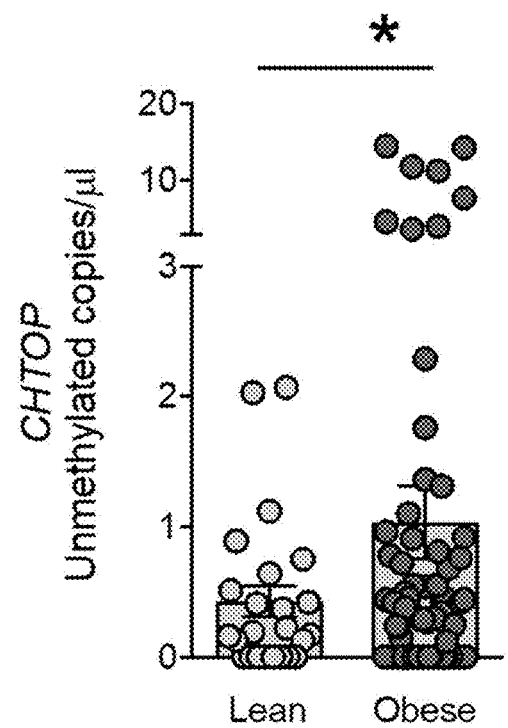
FIGS. 10A-10H presents data for: Circulating CHTOP and INS DNA in youth with obesity and/or T2D. Circulating unmethylated CHTOP DNA in lean and obese youth is presented in FIG. 10A; Circulating methylated CHTOP DNA in lean and obese youth is presented in FIG. 10B; Circulating unmethylated INS DNA in lean and obese youth is presented in FIG. 10C; and circulating methylated INS DNA in lean and obese youth; is presented in FIG. 10D. Circulating unmethylated CHTOP (FIG. 10E) and INS (FIG. 10G) and methylated CHTOP (FIG. 10F) and INS (FIG. 10H) DNA in lean youth with normal glucose tolerance (NGT) and youth with obesity and normal glucose tolerance (OB-NGT), obesity and impaired glucose tolerance (IGT), and clinician-diagnosed obesity with T2D without (T2D-AAb−) and with (T2D-AAb+) autoantibodies. Data are presented as mean±SEM. *P<0.05 for the comparisons indicated.
Figure 10B:
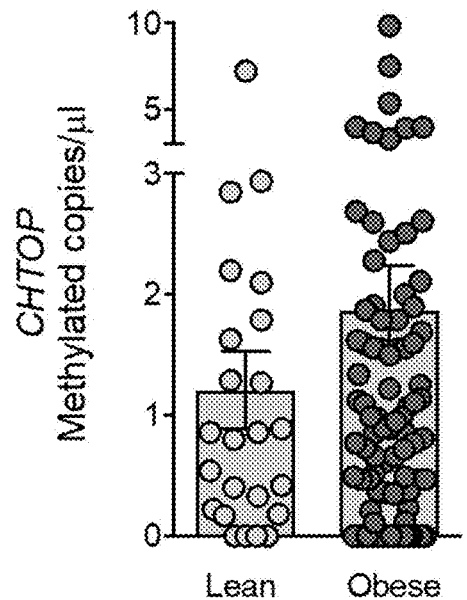
Figure 10C:
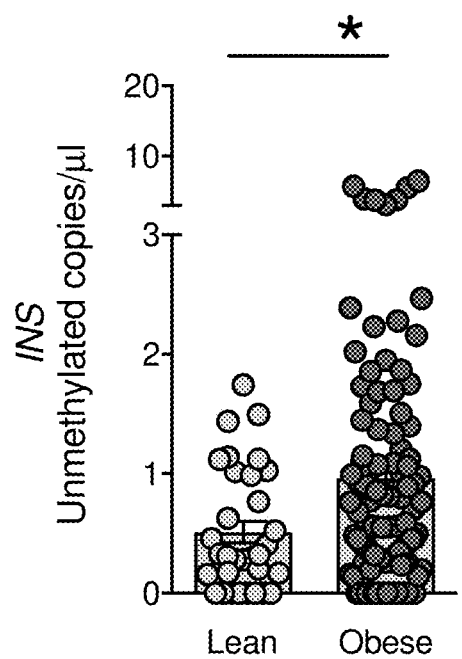
Figure 10D:
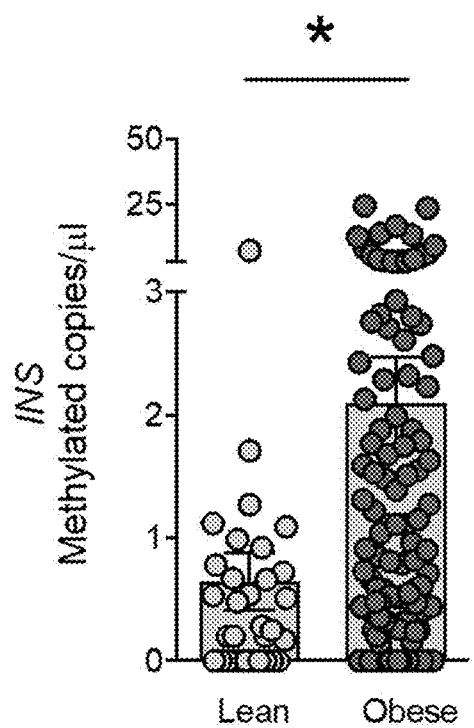
Figure 10E:
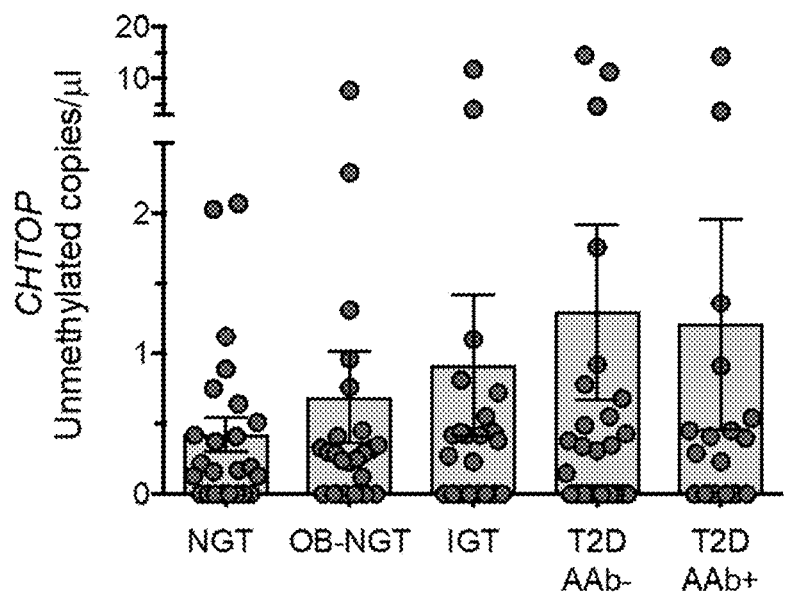
Figure 10F:
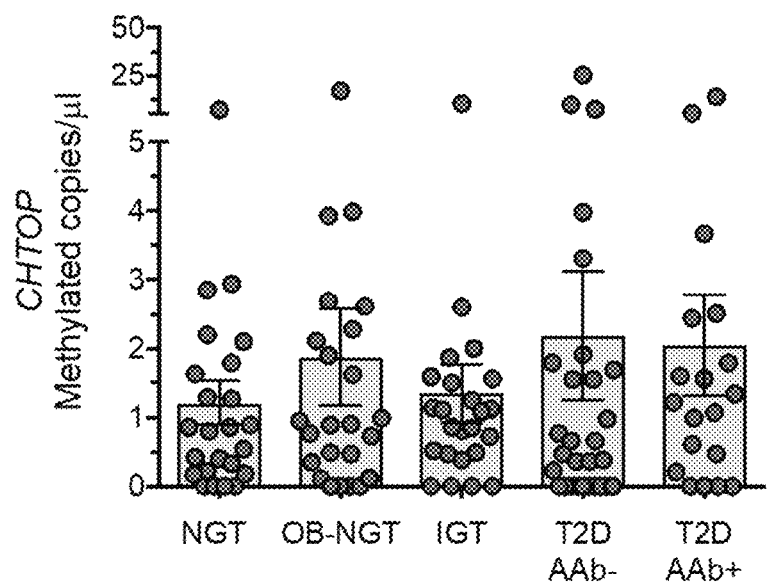
Figure 10G:
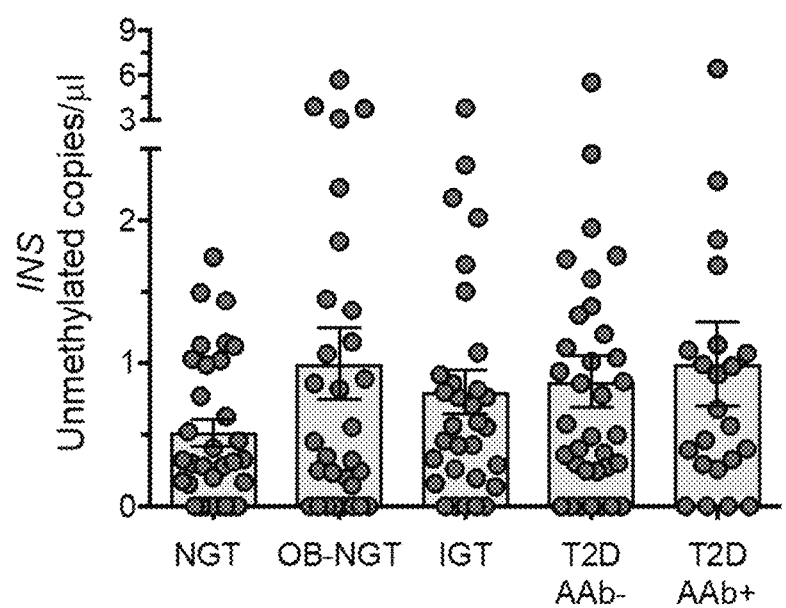
Figure 10H:
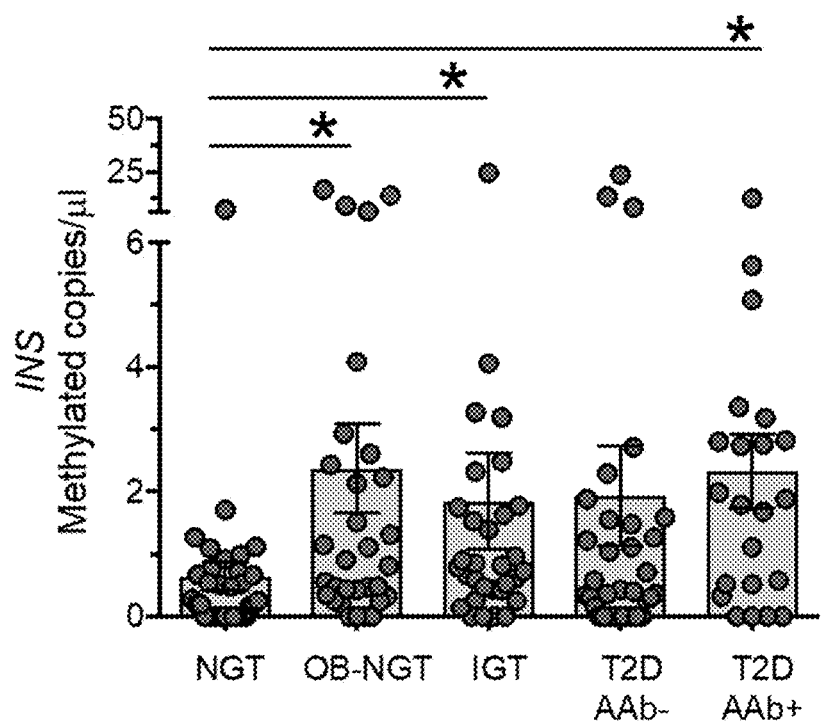

To determine whether our assays could detect islet cell damage associated with insulin resistance, we first measured INS and CHTOP DMD in cohorts of lean and obese children. Obese youth as a group (see clinical characteristics in Table 2) showed significantly higher levels of both unmethylated CHTOP and INS and methylated INS DNA compared to lean control youth, but not methylated CHTOP DNA (FIGS. 10A-10D). To assess if differences in the obese cohort were driven by glycemic control, this cohort was stratified by degree of glucose intolerance: lean controls with normal glucose tolerance (NGT); overweight/obese with normal glucose tolerance (OB-NGT); impaired glucose tolerance (IGT); type 2 diabetes mellitus with and without evidence of islet autoimmunity (T2D, AAb+ and T2D AAB-, respectively). As shown in FIGS. 10E-10H, there were no statistically significant differences in unmethylated CHTOP and INS DNA among these cross-sectional cohorts, suggesting that the overall increases in unmethylated INS in the obese youth cohort reflect a difference driven by obesity alone, and raises the possibility that INS is indicative of systemic stress in the islet, rather than not beta cell death exclusively. Methylated CHTOP DNA was also not different across cohorts (FIG. 10H). By contrast, methylated INS DNA was significantly elevated in obese youth with NGT, IGT, and T2D-AAb+ compared to healthy lean controls (FIG. 10G).

Elevations in Methylated INS and CHTOP DNA are Associated with Systemic Inflammatory States The elevation in cell-free methylated INS in youth with obesity is reminiscent of the elevations we reported in youth with new-onset T1D. Studies interrogating cell-free DNA levels in humans suggest that total cell-free DNA increases with severity of illness in youth. We hypothesized therefore that the elevation in methylated INS in our population might reflect systemic illness. To test this hypothesis, we next applied the DMD assay to serum from youth with severe illness (sepsis requiring intensive care unit-level care) and compared them to age- and sex-matched healthy controls (see Table 3). As shown in FIGS. 6C and 6D, compared to controls, subjects with sepsis exhibited elevations in methylated INS and CHTOP DNA levels but not unmethylated DNA.

Discussion

Measurement of circulating differentially methylated INS DNA has been gaining increased attention as a minimally invasive biomarker of islet cell death that may be used to distinguish individuals with impending and new-onset T1D. However, due to the variability of INS methylation in the islet, and the detection of unmethylated INS DNA in other, non-islet tissues, it cannot be assumed that the signal identified emanates from the islet alone. It is likely that biomarkers in addition to INS based markers will be required to unambiguously detect islet damage. Therefore, we used an unbiased approach to identify another differentially methylated DNA species, CHTOP, that could be utilized to measure islet damage alongside INS, and validated our assays in cohorts of pediatric patients with T1D and T2D.

While increased ratios of unmethylated to methylated INS DNA have been proposed as biomarkers of β-cell death, we showed previously that new-onset T1D youth also exhibit elevated methylated INS. Further, while unmethylated INS DNA is most highly found in islets, tissues, including adipose, contain both methylated and unmethylated INS DNA, thereby highlighting the need for additional biomarkers to confirm islet-specificity. Using an unbiased approach, we identified CHTOP as a gene that was differentially methylated in primary human β cells. We performed DNA deep sequencing in non-islet tissues, primary human β cells, and a well validated human β cell line (EndoC-βH1). Interestingly, CHTOP was found to be hypomethylated in primary human β cells exclusively, and not in the EndoC-βH1 cells. While the reason for this requires further investigation, it is clear that for assessment of differentially methylated biomarker candidate genes, testing should be done in primary human beta cells rather than β cell lines.

While the human INS gene is predominantly unmethylated in the islet, differential methylation is not an all or none phenomenon. Tissues such as skin and adipose are only moderately hypermethylated, and there remains a 40% chance that hypomethylated DNA detected originated in one of those tissues. The CHTOP gene, however, is highly hypermethylated in the skin and adipose. At the same time, tissues that display low or moderate levels of CHTOP methylation are highly methylated in INS DNA. It is only in islets that the hypomethylation signals from INS and CHTOP overlap, indicating that when hypomethylated INS and CHTOP DNA are detected together, we can be confident that the source is islet tissue. In addition to strengthening the use of the existing INS DMD assay, this finding highlights that use of a single differentially methylated gene is unlikely to yield results that are specific and sensitive enough to be used as clinically meaningful biomarkers.

After the development of a CHTOP DMD assay, we validated both the CHTOP and INS DMD assays in youth with new onset T1D who have been shown to have evidence of islet damage at diagnosis. As expected and consistent with our previous work, both unmethylated and methylated INS DNA was elevated in patients with T1D. Similarly, both unmethylated and methylated CHTOP DNA was significantly elevated in new onset T1D patients compared to healthy controls. Surprisingly, however, we also detected significantly elevated levels of unmethylated and methylated INS and CHTOP DNA in first degree relatives of T1D patients who did not have disease and did not have evidence of autoimmunity based on the absence of islet-associated autoantibodies (FDR AAb−). These results demonstrate that differentially methylated INS and CHTOP may reflect islet stress and increased β-cell turnover, rather than β-cell death.

In T2D, the primary etiology of reduced insulin secretion remains unclear. Autopsy studies have demonstrated increases in β-cell mass in adults with obesity and pre-diabetes compared to controls, and lower β cell mass in individuals with frank T2D compared to control. In obese youth, comprehensive autopsy data are not available, but functional data suggest a worsening of β-cell function with increasing dysglycemia. The loss in functional β-cell mass in T2D has been attributed variably to β-cell apoptosis and/or dedifferentiation, but definitive evidence for either is lacking. We first tested our assays in obese youth compared to lean controls and discovered that unmethylated INS and CHTOP were significantly elevated in obese youth, along with methylated INS. The lack of a statistically significant difference in methylated CHTOP is likely secondary to the reduced sensitivity of the assay, as shown in FIGS. 8A-8D. The group of obese subjects was comprised of individuals with varying degrees of insulin resistance and disease. Therefore, we next stratified this obese group across levels of insulin resistance and disease to determine whether a particular disease state was driving the elevations in differentially methylated INS and CHTOP observed. Interestingly, all statistical significance was lost when this group was stratified with the exception of methylated INS, which was significantly elevated in obese subjects with normal and impaired glucose tolerance, and autoantibody positive T2D (FIGS. 10A-10H). These data suggest that methylated INS DNA may reflect states of systemic illness or active assault on the islets by cells with high turnover (i.e. innate immune cells). Similar elevations in methylated INS were observed in pediatric patients admitted to the ICU with sepsis, which would support this hypothesis.

Taken together, our findings identify CHTOP as a new islet-specific DMD that can differentiate new onset T1D patients from controls. Unmethylated CHTOP also distinguishes lean from obese subjects. When used in conjunction with our INS DMD assay, we can more confidently detect islet-specific changes that are observable in cross sectional cohorts of youth with obesity, insulin resistance, and T2D.

What is claimed is:

1. A method for treating inflammation in a subject in need thereof, the method comprising:

identifying a subject suffering from inflammation, wherein said identification is made by detecting preproinsulin DNA having a methylated nucleotide located at position −69 in a first test sample obtained from a test subject;

detecting preproinsulin DNA having an unmethylated nucleotide located at position −69 in a second test sample obtained from said test subject;

comparing the relative concentration of said methylated preproinsulin DNA to said unmethylated preproinsulin DNA in the first and second test sample with the relative concentration of preproinsulin DNA having a methylated nucleotide located at position −69 to preproinsulin DNA having an unmethylated nucleotide located at position −69 in a control;

detecting methylated CHTOP DNA in a third test sample obtained from the test subject;

detecting unmethylated CHTOP DNA in a fourth sample obtained from the subject suspected of having inflammation;

comparing the relative concentration of methylated CHTOP DNA to unmethylated CHTOP DNA in the third and fourth test sample with the relative concentration of methylated CHTOP DNA to unmethylated CHTOP DNA in a control;

detecting a relative concentration of said methylated preproinsulin DNA in said first test sample that is greater than the relative concentration of said methylated preproinsulin DNA in the control and detecting a relative concentration of methylated CHTOP DNA in said third test sample that is greater than the relative concentration of methylated CHTOP DNA in the control and fourth test sample; and determining the subject has inflammation; and administering an anti-inflammatory drug selected from the group consisting of a nonsteroidal anti-inflammatory drug, a corticosteroid and immune-suppressant drug to said subject identified as suffering from inflammation.

2. The method of claim 1, wherein the preproinsulin DNA in the first and second test sample and the CHTOP DNA in the third and fourth test sample is subjected to a bisulfite reaction.

3. The method of claim 2, wherein the first, second, third and fourth test sample is selected from the group consisting of serum, plasma, whole blood, and urine.

4. The method of claim 1 wherein the inflammation is due to sepsis and detection of the inflammation identifies a subject as having sepsis.

5. The method of claim 1 wherein the nonsteroidal anti-inflammatory drug is aspirin, ibuprofen, or Celebrex and the corticosteroid is prednisone.

* * * * *